(12) United States Patent
Willis et al.

(10) Patent No.: US 11,134,835 B2
(45) Date of Patent: *Oct. 5, 2021

(54) ENDOSCOPIC VESSEL HARVESTING SYSTEM COMPONENTS

(71) Applicant: MAQUET CARDIOVASCULAR LLC, San Jose, CA (US)

(72) Inventors: Geoffrey H. Willis, Mountain View, CA (US); Ryan C. Abbott, San Jose, CA (US)

(73) Assignee: MAQUET CARDIOVASCULAR LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/404,656

(22) Filed: May 6, 2019

(65) Prior Publication Data
US 2019/0254645 A1    Aug. 22, 2019

Related U.S. Application Data

(62) Division of application No. 15/686,046, filed on Aug. 24, 2017, now Pat. No. 10,299,770, which is a (Continued)

(51) Int. Cl.
*A61B 18/14*    (2006.01)
*A61B 1/313*    (2006.01)
(Continued)

(52) U.S. Cl.
CPC ........ *A61B 1/3137* (2013.01); *A61B 1/00089* (2013.01); *A61B 1/00096* (2013.01);
(Continued)

(58) Field of Classification Search
CPC ... A61B 17/00008; A61B 90/70; A61B 1/313; A61B 1/00089; A61B 1/00096;
(Continued)

(56) References Cited

U.S. PATENT DOCUMENTS

| | | |
|---|---|---|
| 1,083,386 A | 1/1914 | Chapman |
| 1,422,826 A | 7/1922 | Brown |

(Continued)

FOREIGN PATENT DOCUMENTS

| | | |
|---|---|---|
| AU | 199717100 B2 | 8/1997 |
| AU | 199717100 B2 | 10/1997 |

(Continued)

OTHER PUBLICATIONS

Non-Final Office Action issued in U.S. Appl. No. 15/686,703, dated Dec. 27, 2018.

(Continued)

*Primary Examiner* — Thomas A Giuliani
(74) *Attorney, Agent, or Firm* — Wesley Scott Ashton

(57) ABSTRACT

A vessel dissector used in conjunction with an endoscope is provided with a lumen for receiving the endoscope; a blunt dissecting tip provided on a distal end of an elongated cannula permitting tissue dissection while viewing internal body structures via an objective lens of the endoscope; and a vessel severing tool extending through at least a portion of the elongated cannula and translatable longitudinally relative to the elongated cannula, and the vessel severing tool comprises an electrode-carrying member translatable circumferentially within an arcuate slot extending through an outer surface of the vessel dissector, wherein the arcuate slot comprises an inner radius, an outer radius and a central radius, wherein the outer radius is greater than the inner radius and the central radius is located between the outer radius and the inner radius so the arcuate slot provides a uniform opening through which the electrode-carrying member can extend and retract.

16 Claims, 10 Drawing Sheets

Related U.S. Application Data division of application No. 11/446,024, filed on Jun. 1, 2006, now Pat. No. 9,770,230.

(51) Int. Cl.

| | |
|---|---|
| *A61B 1/00* | (2006.01) |
| *A61B 1/018* | (2006.01) |
| *A61B 17/00* | (2006.01) |
| *A61B 1/12* | (2006.01) |
| *A61B 17/32* | (2006.01) |
| *A61B 90/00* | (2016.01) |
| *A61B 90/70* | (2016.01) |

(52) U.S. Cl.
CPC .......... *A61B 1/00135* (2013.01); *A61B 1/018* (2013.01); *A61B 1/313* (2013.01); *A61B 17/00008* (2013.01); *A61B 1/126* (2013.01); *A61B 90/361* (2016.02); *A61B 90/70* (2016.02); *A61B 2017/320044* (2013.01)

(58) Field of Classification Search
CPC ........ A61B 1/018; A61B 2017/320044; A61B 2017/320052; A61B 2018/00196; A61B 2018/00202; A61B 2018/00404; A61B 2018/00428; A61B 2018/00607; A61B 2018/00982; A61B 2018/1465; A61B 2018/1475
USPC ............. 606/41, 45–52, 159, 205, 206, 209; 600/205; 607/98, 99, 113, 115, 116
See application file for complete search history.

(56) References Cited

U.S. PATENT DOCUMENTS

| | | |
|---|---|---|
| 1,683,708 A | 9/1928 | Wappler et al. |
| 1,727,495 A | 12/1928 | Wappler |
| 1,731,069 A | 12/1928 | Herman |
| 1,741,461 A | 12/1929 | Herman |
| 1,798,902 A | 3/1931 | Raney |
| 1,867,624 A | 7/1932 | Hoffman |
| 1,881,250 A | 10/1932 | Tomlinson |
| 1,978,495 A | 10/1934 | Landau |
| 2,001,169 A | 5/1935 | Wallace |
| 2,002,594 A | 5/1935 | Wappler et al. |
| 2,004,559 A | 6/1935 | Wappler |
| 2,011,169 A | 8/1935 | Wappler |
| 2,012,937 A | 9/1935 | Beuoy |
| 2,028,635 A | 1/1936 | Wappler |
| 2,031,682 A | 2/1936 | Wappler et al. |
| 2,162,681 A | 6/1939 | Oval |
| 2,220,720 A | 11/1940 | Jett |
| 2,227,727 A | 1/1941 | Leggiadro |
| 2,316,297 A | 4/1943 | Southerland et al. |
| 2,821,190 A | 1/1958 | Chase |
| 2,840,070 A | 6/1958 | Tofflemire |
| 2,868,206 A | 1/1959 | Stoesser |
| 2,944,552 A | 7/1960 | Cannon |
| 3,168,096 A | 2/1965 | Brummelkamp |
| 3,185,155 A | 5/1965 | Slaten et al. |
| 3,200,028 A | 8/1965 | Chisholm |
| 3,224,320 A | 12/1965 | Knudsen |
| 3,297,022 A | 1/1967 | Wallace |
| 3,313,294 A | 4/1967 | Uddenberg |
| 3,336,916 A | 8/1967 | Edlich |
| 3,354,478 A | 11/1967 | Allen |
| 3,357,433 A | 12/1967 | Fourestier et al. |
| 3,391,690 A | 7/1968 | Armao |
| 3,439,523 A | 4/1969 | Wood |
| 3,568,677 A | 3/1971 | Nolan et al. |
| 3,613,682 A | 10/1971 | Naylor |
| 3,625,202 A | 12/1971 | Oyoshirhara |
| 3,772,127 A | 11/1973 | James |
| 3,805,793 A | 4/1974 | Wright |
| 3,835,841 A | 9/1974 | Terada |
| 3,856,016 A | 12/1974 | Davis |
| 3,857,386 A | 12/1974 | Ashbell |
| 3,866,599 A | 2/1975 | Johnson |
| 3,866,601 A | 2/1975 | Russell |
| 3,882,852 A | 5/1975 | Sinnreich |
| 3,882,854 A | 5/1975 | Hulka et al. |
| 3,929,137 A | 12/1975 | Gonser |
| 3,934,115 A | 1/1976 | Peterson |
| 3,938,527 A | 2/1976 | Rioux et al. |
| 3,980,861 A | 9/1976 | Fukunaga |
| RE29,088 E | 12/1976 | Shaw |
| 4,011,872 A | 3/1977 | Komiya |
| 4,030,743 A | 6/1977 | Warthen |
| 4,031,898 A | 6/1977 | Hiltebrandt et al. |
| 4,038,987 A | 8/1977 | Komiya |
| 4,052,980 A | 10/1977 | Grams et al. |
| 4,132,227 A | 1/1979 | Ibe |
| 4,175,545 A | 11/1979 | Termanini |
| 4,178,920 A | 12/1979 | Cawood et al. |
| 4,190,042 A | 2/1980 | Sinnreich |
| 4,196,734 A | 4/1980 | Harris |
| 4,213,460 A | 7/1980 | Weiner |
| 4,232,660 A | 11/1980 | Coles |
| 1,248,214 A | 2/1981 | Hannah et al. |
| 4,257,420 A | 3/1981 | Terayama |
| 4,285,753 A | 8/1981 | Warthen |
| 4,315,510 A | 2/1982 | Kihn |
| 4,359,052 A | 11/1982 | Staub |
| 4,362,160 A | 12/1982 | Hiltebrandt |
| 4,369,768 A | 1/1983 | Vukovic |
| 4,370,980 A | 2/1983 | Lottick |
| 4,372,295 A | 2/1983 | Heckele |
| 4,418,692 A | 12/1983 | Guay |
| 4,423,727 A | 1/1984 | Widran et al. |
| 4,428,746 A | 1/1984 | Mendez |
| 4,436,087 A | 3/1984 | Ouchi |
| 4,440,170 A | 4/1984 | Golden et al. |
| 4,493,320 A | 1/1985 | Treat |
| 4,493,321 A | 1/1985 | Leather |
| 4,493,711 A | 1/1985 | Chin et al. |
| 4,499,898 A | 2/1985 | Knepshield et al. |
| 4,499,899 A | 2/1985 | Lyons, III |
| 4,516,574 A | 5/1985 | Hewes, Jr. |
| 4,516,575 A | 5/1985 | Gerhard et al. |
| 4,556,058 A | 12/1985 | Green |
| 4,557,255 A | 12/1985 | Goodman |
| 4,562,832 A | 1/1986 | Wilder et al. |
| 4,586,919 A | 5/1986 | Taheri |
| 4,587,968 A | 5/1986 | Price |
| 4,597,030 A | 6/1986 | Brody et al. |
| 4,597,379 A | 7/1986 | Kihn et al. |
| 4,597,389 A | 7/1986 | Ibrahim et al. |
| 4,600,940 A | 7/1986 | Sluyter |
| 4,607,622 A | 8/1986 | Fritch et al. |
| 4,638,802 A | 1/1987 | Okada |
| 4,646,738 A | 3/1987 | Trott |
| 4,649,917 A | 3/1987 | Karasawa |
| 4,651,733 A | 3/1987 | Mobin Uddin |
| 4,653,476 A | 3/1987 | Bonnet |
| 4,654,024 A | 3/1987 | Crittenden et al. |
| 4,655,216 A | 4/1987 | Tischer |
| 4,656,999 A | 4/1987 | Storz |
| 4,657,018 A | 4/1987 | Hakky |
| 4,662,068 A | 5/1987 | Polonsky |
| 4,667,655 A | 5/1987 | Ogiu et al. |
| 4,671,274 A | 6/1987 | Sorochenko |
| 4,700,694 A | 10/1987 | Shishido |
| 4,702,246 A | 10/1987 | Ellis et al. |
| 4,705,041 A | 11/1987 | Kim |
| 4,726,355 A | 2/1988 | Okada |
| 4,726,370 A | 2/1988 | Karasawa et al. |
| 4,744,363 A | 5/1988 | Hasson |
| 4,745,908 A | 5/1988 | Wardle |
| 4,754,754 A | 7/1988 | Garito et al. |
| 4,759,348 A | 7/1988 | Cawood |
| 4,759,364 A | 7/1988 | Boebel |
| 4,762,120 A | 8/1988 | Hussein |
| 4,768,508 A | 9/1988 | Chin et al. |

(56) References Cited

U.S. PATENT DOCUMENTS

| | | |
|---|---|---|
| 4,772,093 A | 9/1988 | Abele et al. |
| 4,773,394 A | 9/1988 | Reichstein et al. |
| 4,779,611 A | 10/1988 | Grooters et al. |
| 4,793,346 A | 12/1988 | Mindich |
| 4,819,620 A | 4/1989 | Okutsu |
| 4,819,633 A | 4/1989 | Bauer et al. |
| 4,821,718 A | 4/1989 | Uldall |
| 4,838,246 A | 6/1989 | Hahn et al. |
| 4,858,595 A | 8/1989 | Buess et al. |
| 4,862,874 A | 9/1989 | Kellner |
| 4,865,019 A | 9/1989 | Phillips |
| 4,867,138 A | 9/1989 | Kubota et al. |
| 4,869,268 A | 9/1989 | Yoon |
| 4,874,375 A | 10/1989 | Ellison |
| 4,877,016 A | 10/1989 | Kantor et al. |
| 4,919,129 A | 4/1990 | Weber et al. |
| 4,924,851 A | 5/1990 | Ognier et al. |
| 4,924,882 A | 5/1990 | Donovan |
| 4,931,042 A | 6/1990 | Holmes et al. |
| 4,932,952 A | 6/1990 | Wojciechowicz, Jr. |
| 4,936,842 A | 6/1990 | D'Amelio et al. |
| 4,950,278 A | 8/1990 | Sachse et al. |
| 4,959,067 A | 9/1990 | Muller |
| 4,966,596 A | 10/1990 | Kuntz et al. |
| 4,979,771 A | 12/1990 | Childs, III |
| 4,985,030 A | 1/1991 | Melzer et al. |
| 4,991,565 A | 2/1991 | Takahashi et al. |
| 4,994,062 A | 2/1991 | Nishigaki et al. |
| 4,997,419 A | 3/1991 | Lakatos et al. |
| 4,997,436 A | 3/1991 | Oberlander |
| 4,998,527 A | 3/1991 | Meyer |
| 4,998,972 A | 3/1991 | Chin et al. |
| 5,007,898 A | 4/1991 | Rosenbluth et al. |
| 5,007,907 A | 4/1991 | Nishigaki et al. |
| 5,007,908 A | 4/1991 | Rydell |
| 5,011,490 A | 4/1991 | Fischell et al. |
| 5,013,312 A | 5/1991 | Parins et al. |
| 5,020,514 A | 6/1991 | Heckele |
| 5,025,778 A | 6/1991 | Silverstein et al. |
| 5,026,370 A | 6/1991 | Lottick |
| 5,026,383 A | 6/1991 | Nobles |
| 5,035,232 A | 7/1991 | Lutze et al. |
| 5,037,433 A | 8/1991 | Wilk et al. |
| 5,046,251 A | 9/1991 | Scott |
| 5,047,038 A | 9/1991 | Peters et al. |
| 5,049,154 A | 9/1991 | Quadri |
| 5,053,041 A | 10/1991 | Ansari et al. |
| 5,100,420 A | 3/1992 | Green et al. |
| 5,122,137 A | 6/1992 | Lennox |
| 5,139,508 A | 8/1992 | Kantrowitz et al. |
| 5,147,356 A | 9/1992 | Bhatta |
| 5,151,096 A | 9/1992 | Khoury |
| 5,151,102 A | 9/1992 | Kamiyama et al. |
| 5,171,255 A | 12/1992 | Rydell |
| 5,171,311 A | 12/1992 | Rydell et al. |
| 5,181,919 A | 1/1993 | Bergman et al. |
| 5,188,630 A | 2/1993 | Christoudias |
| 5,190,541 A | 3/1993 | Abele et al. |
| 5,192,280 A | 3/1993 | Parins |
| 5,197,649 A | 3/1993 | Bessler et al. |
| 5,197,971 A | 3/1993 | Bonutti |
| 5,201,752 A | 4/1993 | Brown et al. |
| 5,203,773 A | 4/1993 | Green |
| 5,207,691 A | 5/1993 | Nardella |
| 5,213,093 A | 5/1993 | Swindle |
| 5,217,001 A | 6/1993 | Nakao et al. |
| 5,217,441 A | 6/1993 | Shichman |
| 5,217,458 A | 6/1993 | Parins |
| 5,226,890 A | 7/1993 | Ianniruberto et al. |
| 5,226,908 A | 7/1993 | Yoon |
| 5,230,621 A | 7/1993 | Jacoby |
| 5,250,046 A | 10/1993 | Lee |
| 5,251,613 A | 10/1993 | Adair |
| 5,258,006 A | 11/1993 | Rydell et al. |
| 5,259,366 A | 11/1993 | Reydel et al. |
| 5,267,998 A | 12/1993 | Hagen |
| 5,269,753 A | 12/1993 | Wilk |
| 5,269,785 A | 12/1993 | Bonutti |
| 5,271,380 A | 12/1993 | Riek et al. |
| 5,271,385 A | 12/1993 | Bailey |
| 5,273,026 A | 12/1993 | Wilk |
| 5,275,608 A | 1/1994 | Forman et al. |
| 5,276,306 A | 1/1994 | Huffman |
| 5,279,546 A | 1/1994 | Mische et al. |
| 5,279,565 A | 1/1994 | Klein et al. |
| 5,284,128 A | 2/1994 | Hart |
| 5,284,478 A | 2/1994 | Nobles et al. |
| 5,290,249 A | 3/1994 | Foster et al. |
| 5,290,284 A | 3/1994 | Adair |
| 5,290,286 A | 3/1994 | Parins |
| 5,295,994 A | 3/1994 | Bonutti |
| 5,300,036 A | 4/1994 | Mueller et al. |
| 5,312,423 A | 5/1994 | Rosenbluth et al. |
| 5,318,564 A | 6/1994 | Eggers |
| 5,318,586 A | 6/1994 | Ereren |
| 5,320,115 A | 6/1994 | Kenna |
| 5,322,503 A | 6/1994 | Desai |
| 5,330,497 A | 7/1994 | Freitas et al. |
| 5,334,150 A | 8/1994 | Kaali |
| 5,336,221 A | 8/1994 | Anderson |
| 5,336,229 A | 8/1994 | Noda |
| 5,336,231 A | 8/1994 | Adair |
| 5,337,736 A | 8/1994 | Reddy |
| 5,339,803 A | 8/1994 | Mayzels et al. |
| 5,345,927 A | 9/1994 | Bonutti |
| 5,346,504 A | 9/1994 | Ortiz et al. |
| 5,352,219 A | 10/1994 | Reddy |
| 5,352,222 A | 10/1994 | Rydell |
| 5,354,291 A | 10/1994 | Bales et al. |
| 5,359,995 A | 11/1994 | Sewell, Jr. |
| 5,360,428 A | 11/1994 | Hutchinson, Jr. |
| 5,366,476 A | 11/1994 | Noda |
| 5,368,015 A | 11/1994 | Wilk |
| 5,370,109 A | 12/1994 | Cuny |
| 5,373,840 A | 12/1994 | Knighton |
| 5,374,277 A | 12/1994 | Hassler |
| 5,376,076 A | 12/1994 | Kaali |
| 5,376,087 A | 12/1994 | Haber et al. |
| 5,380,291 A | 1/1995 | Kaali |
| 5,383,889 A | 1/1995 | Warner et al. |
| 5,385,572 A | 1/1995 | Nobles et al. |
| 5,386,817 A | 2/1995 | Jones ................ A61B 1/00091 138/108 |
| 5,386,818 A | 2/1995 | Schneebaum et al. |
| 5,389,098 A | 2/1995 | Tsuruta et al. |
| 5,391,178 A | 2/1995 | Yapor |
| 5,395,367 A | 3/1995 | Wilk |
| 5,395,383 A | 3/1995 | Adams et al. |
| 5,397,335 A | 3/1995 | Gresl et al. |
| 5,401,273 A | 3/1995 | Shippert |
| 5,403,312 A | 4/1995 | Yates et al. |
| 5,411,466 A | 5/1995 | Hess |
| 5,411,483 A | 5/1995 | Loomas et al. |
| 5,411,508 A | 5/1995 | Bessler et al. |
| 5,417,697 A | 5/1995 | Wilk et al. |
| 5,419,309 A | 5/1995 | Biehl |
| 5,445,638 A | 5/1995 | Rydell |
| 5,423,321 A | 6/1995 | Fontenot |
| 5,423,813 A | 6/1995 | Kaiser et al. |
| 5,424,877 A | 6/1995 | Tsuyuki et al. |
| 5,425,355 A | 6/1995 | Kulick |
| 5,425,357 A | 6/1995 | Moll et al. |
| 5,431,151 A | 7/1995 | Riek et al. |
| 5,441,041 A | 8/1995 | Sauer et al. |
| 5,441,044 A | 8/1995 | Tovey et al. |
| 5,441,497 A | 8/1995 | Narciso, Jr. |
| 5,441,498 A | 8/1995 | Perkins |
| 5,443,463 A | 8/1995 | Stern et al. |
| 5,447,502 A | 9/1995 | Haaga |
| 5,447,513 A | 9/1995 | Davison et al. |
| 5,448,990 A | 9/1995 | De Faria Correa |
| 5,450,842 A | 9/1995 | Tovey et al. |
| 5,451,223 A | 9/1995 | Ben-Simhon |
| 5,452,513 A | 9/1995 | Zinnbauer et al. |

(56) References Cited

U.S. PATENT DOCUMENTS

| | | |
|---|---|---|
| 5,452,732 A | 9/1995 | Bircoll |
| 5,454,365 A | 10/1995 | Bonutti |
| 5,458,598 A | 10/1995 | Feinberg et al. |
| 5,460,629 A | 10/1995 | Shlain et al. |
| 5,468,248 A | 11/1995 | Chin et al. |
| 5,474,057 A | 12/1995 | Makower et al. |
| 5,480,409 A | 1/1996 | Riza |
| 5,486,155 A | 1/1996 | Muller et al. |
| 5,489,290 A | 2/1996 | Furnish |
| 5,490,836 A | 2/1996 | Desai |
| 5,496,317 A | 3/1996 | Goble et al. |
| 5,496,345 A | 3/1996 | Kieturakis et al. |
| 5,501,654 A | 3/1996 | Failla et al. |
| 5,505,686 A | 4/1996 | Willis et al. |
| 5,507,755 A | 4/1996 | Gresl et al. |
| 5,509,922 A | 4/1996 | Aranyi et al. |
| 5,511,564 A | 4/1996 | Wilk |
| 5,512,037 A | 4/1996 | Russell et al. |
| 5,512,721 A | 4/1996 | Young et al. |
| 5,514,084 A | 5/1996 | Fisher |
| 5,514,151 A | 5/1996 | Fogarty et al. |
| 5,514,153 A | 5/1996 | Bonutti |
| 5,514,236 A | 5/1996 | Avellanet et al. |
| 5,522,788 A | 6/1996 | Kuzmak |
| 5,522,830 A | 6/1996 | Aranyi |
| 5,527,331 A | 6/1996 | Kresch et al. |
| 5,533,496 A | 7/1996 | De Faria Correa et al. |
| 5,535,759 A | 7/1996 | Wilk |
| 5,536,251 A | 7/1996 | Evard et al. |
| 5,540,711 A | 7/1996 | Kieturakis et al. |
| 5,549,605 A | 8/1996 | Hahnen |
| 5,549,636 A | 8/1996 | Li |
| 5,549,637 A | 8/1996 | Crainich |
| 5,551,947 A | 9/1996 | Kaali |
| 5,554,101 A | 9/1996 | Matula et al. |
| 5,556,563 A | 9/1996 | von der Heyde et al. |
| 5,558,620 A | 9/1996 | Heckele et al. |
| 5,564,615 A | 10/1996 | Bishop et al. |
| 5,565,122 A | 10/1996 | Zinnbauer et al. |
| 5,569,160 A | 10/1996 | Sauer et al. |
| 5,569,164 A | 10/1996 | Lurz |
| 5,569,183 A | 10/1996 | Kieturakis |
| 5,569,244 A | 10/1996 | Hahnen |
| 5,569,274 A | 10/1996 | Rapacki et al. |
| 5,569,291 A | 10/1996 | Privitera et al. |
| 5,571,100 A | 11/1996 | Goble |
| 5,575,756 A | 11/1996 | Karasawa et al. |
| 5,582,611 A | 12/1996 | Tsuruta et al. |
| 5,588,581 A | 12/1996 | Conlon et al. |
| 5,591,183 A | 1/1997 | Chin |
| 5,591,186 A | 1/1997 | Wurster et al. |
| 5,593,418 A | 1/1997 | Mollenauer |
| 5,595,565 A | 1/1997 | Treat et al. |
| 5,599,305 A | 2/1997 | Hermann et al. |
| 5,599,349 A | 2/1997 | D'Amelio |
| 5,601,580 A | 2/1997 | Goldberg et al. |
| 5,601,581 A | 2/1997 | Fogarty et al. |
| 5,601,589 A | 2/1997 | Fogarty et al. |
| 5,601,601 A | 2/1997 | Tal et al. |
| 5,603,698 A | 2/1997 | Roberts et al. |
| 5,607,441 A | 3/1997 | Sierocuk et al. |
| 5,607,443 A | 3/1997 | Kieturakis et al. |
| 5,618,307 A | 4/1997 | Donlon et al. |
| 5,626,587 A | 5/1997 | Bishop et al. |
| 5,630,787 A | 5/1997 | Yabe et al. |
| 5,630,795 A | 5/1997 | Kuramoto et al. |
| 5,634,584 A | 6/1997 | Okorocha et al. |
| 5,634,924 A | 6/1997 | Turkel et al. |
| 5,647,871 A | 7/1997 | Levine et al. |
| 5,653,722 A | 8/1997 | Kieturakis |
| 5,653,726 A | 8/1997 | Kieturakis |
| 5,656,012 A | 8/1997 | Sienkiewicz |
| 5,658,282 A | 8/1997 | Daw et al. |
| 5,662,585 A | 9/1997 | Willis et al. |
| 5,662,588 A | 9/1997 | Iida |
| 5,662,662 A | 9/1997 | Bishop et al. |
| 5,665,085 A | 9/1997 | Nardella |
| 5,665,096 A | 9/1997 | Yoon |
| 5,665,100 A | 9/1997 | Yoon |
| 5,667,480 A | 9/1997 | Knight et al. |
| 5,667,520 A | 9/1997 | Bonutti |
| 5,669,906 A | 9/1997 | Grossi et al. |
| 5,673,840 A | 10/1997 | Schulze et al. |
| 5,680,982 A | 10/1997 | Schulze et al. |
| 5,683,349 A | 11/1997 | Makower et al. |
| 5,685,820 A | 11/1997 | Riek et al. |
| 5,685,826 A | 11/1997 | Bonutti |
| 5,688,269 A | 11/1997 | Newton et al. |
| 5,688,270 A | 11/1997 | Yates et al. |
| 5,688,286 A | 11/1997 | Yoon |
| 5,690,606 A | 11/1997 | Slotman |
| 5,690,847 A | 11/1997 | LaValley et al. |
| 5,693,051 A | 12/1997 | Schulze et al. |
| 5,695,448 A | 12/1997 | Kimura et al. |
| 5,700,236 A | 12/1997 | Sauer et al. |
| 5,702,408 A | 12/1997 | Wales et al. |
| 5,702,412 A | 12/1997 | Popov et al. |
| 5,702,417 A | 12/1997 | Hermann |
| 5,704,372 A | 1/1998 | Moll et al. |
| 5,704,534 A | 1/1998 | Huitema et al. |
| 5,707,382 A | 1/1998 | Sierocuk et al. |
| 5,707,389 A | 1/1998 | Louw et al. |
| 5,707,390 A | 1/1998 | Bonutti |
| 5,709,680 A | 1/1998 | Yates et al. |
| 5,713,505 A | 2/1998 | Huitema |
| 5,716,325 A | 2/1998 | Bonutti |
| 5,716,352 A | 2/1998 | Viola et al. |
| 5,718,714 A | 2/1998 | Livneh |
| 5,720,761 A | 2/1998 | Kaali |
| 5,720,763 A | 2/1998 | Tovey |
| 5,722,934 A | 3/1998 | Knight et al. |
| 5,725,479 A | 3/1998 | Knight et al. |
| 5,728,119 A | 3/1998 | Smith et al. |
| 5,730,748 A | 3/1998 | Fogarty et al. |
| 5,730,756 A | 3/1998 | Kieturakis et al. |
| 5,735,848 A | 4/1998 | Yates et al. |
| 5,738,628 A | 4/1998 | Sierocuk et al. |
| 5,743,880 A | 4/1998 | Hlavka |
| 5,749,870 A | 5/1998 | Gloth et al. |
| 5,752,966 A | 5/1998 | Chang |
| 5,755,717 A | 5/1998 | Yates et al. |
| 5,759,150 A | 6/1998 | Konou et al. |
| 5,759,183 A | 6/1998 | VanDusseldorp |
| 5,759,188 A | 6/1998 | Yoon |
| 5,762,606 A | 6/1998 | Minnich |
| 5,766,169 A | 6/1998 | Fritzsch et al. |
| 5,766,215 A | 6/1998 | Muri et al. |
| 5,772,576 A | 6/1998 | Knighton et al. |
| 5,776,112 A | 7/1998 | Stephens et al. |
| 5,779,646 A | 7/1998 | Koblish et al. |
| 5,779,728 A | 7/1998 | Lunsford et al. |
| 5,795,331 A | 8/1998 | Cragg et al. |
| 5,797,907 A | 8/1998 | Clement |
| 5,797,920 A | 8/1998 | Kim |
| 5,807,393 A | 9/1998 | Williamson et al. |
| 5,810,811 A | 9/1998 | Yates et al. |
| 5,814,016 A | 9/1998 | Valley et al. |
| 5,817,013 A | 10/1998 | Ginn et al. |
| 5,817,061 A | 10/1998 | Goodwin et al. |
| 5,817,062 A | 10/1998 | Flom et al. |
| 5,823,947 A | 10/1998 | Yoon et al. |
| 5,827,279 A | 10/1998 | Hughett et al. |
| 5,827,281 A | 10/1998 | Levin |
| 5,827,318 A | 10/1998 | Bonutti |
| 5,832,931 A | 11/1998 | Wachter et al. |
| 5,843,017 A | 12/1998 | Yoon |
| 5,843,121 A | 12/1998 | Yoon |
| RE36,043 E | 1/1999 | Knighton |
| 5,857,961 A | 1/1999 | Vanden Hoek et al. |
| 5,860,997 A | 1/1999 | Bonutti |
| 5,865,802 A | 2/1999 | Yoon et al. |
| 5,868,785 A | 2/1999 | Tal et al. |
| 5,871,496 A | 2/1999 | Ginn et al. |
| 5,871,498 A | 2/1999 | Jervis et al. |

(56) References Cited

U.S. PATENT DOCUMENTS

| | | |
|---|---|---|
| 5,873,828 A | 2/1999 | Fujio et al. |
| 5,873,889 A | 2/1999 | Chin |
| 5,895,352 A | 4/1999 | Kleiner |
| 5,895,353 A | 4/1999 | Lunsford et al. |
| 5,897,487 A | 4/1999 | Ouchi |
| 5,908,429 A | 6/1999 | Yoon |
| 5,913,870 A | 6/1999 | DeFonzo et al. |
| 5,914,062 A | 6/1999 | von der Heyde |
| 5,916,213 A | 6/1999 | Haissaguerre et al. |
| 5,916,233 A * | 6/1999 | Chin .............. A61B 17/00008 606/190 |
| 5,919,191 A * | 7/1999 | Lennox ............... A61B 18/14 606/46 |
| 5,921,993 A | 7/1999 | Yoon |
| 5,925,058 A | 7/1999 | Smith et al. |
| 5,928,135 A | 7/1999 | Knight et al. |
| 5,928,138 A | 7/1999 | Knight et al. |
| 5,928,264 A | 7/1999 | Sugarbaker et al. |
| 5,938,620 A | 8/1999 | Daxer |
| 5,944,732 A | 8/1999 | Raulerson et al. |
| 5,954,731 A | 9/1999 | Yoon |
| 5,957,923 A | 9/1999 | Hahnen et al. |
| 5,957,936 A | 9/1999 | Yoon et al. |
| 5,976,130 A | 11/1999 | McBrayer et al. |
| 5,980,549 A | 11/1999 | Chin |
| 5,984,937 A | 11/1999 | Morse et al. |
| 5,984,938 A | 11/1999 | Yoon |
| 5,984,939 A | 11/1999 | Yoon |
| 5,993,384 A | 11/1999 | Lunsford et al. |
| 5,997,570 A | 12/1999 | Ligtenberg et al. |
| 6,015,423 A | 1/2000 | Andrese |
| 6,036,713 A | 3/2000 | Kieturakis |
| 6,059,802 A | 5/2000 | Ginn |
| 6,071,232 A | 6/2000 | Knighton et al. |
| 6,077,277 A | 6/2000 | Mollenauer et al. |
| 6,080,102 A | 6/2000 | Konou et al. |
| 6,120,434 A | 9/2000 | Kimura et al. |
| 6,123,689 A | 9/2000 | To et al. |
| H1904 H | 10/2000 | Yates et al. |
| 6,129,661 A | 10/2000 | Iafrati et al. |
| 6,143,008 A | 11/2000 | Eaves, III ........ A61B 17/00008 606/159 |
| 6,162,173 A | 12/2000 | Chin et al. |
| 6,167,297 A | 12/2000 | Benaron |
| 6,174,307 B1 | 1/2001 | Daniel et al. |
| 6,176,825 B1 | 1/2001 | Chin et al. |
| 6,186,825 B1 | 2/2001 | Bogiel et al. |
| 6,193,653 B1 | 2/2001 | Evans .............. A61B 17/00008 600/210 |
| 6,196,968 B1 | 3/2001 | Rydin et al. |
| 6,206,823 B1 | 3/2001 | Kolata et al. |
| 6,206,899 B1 | 3/2001 | Ginn |
| 6,224,555 B1 | 5/2001 | Ouchi |
| 6,228,025 B1 | 5/2001 | Hipps et al. |
| 6,234,958 B1 | 5/2001 | Snoke et al. |
| 6,270,492 B1 | 8/2001 | Sinofsky |
| 6,277,137 B1 | 8/2001 | Chin |
| 6,287,304 B1 | 9/2001 | Eggers et al. |
| 6,306,081 B1 | 10/2001 | Ishikawa et al. |
| 6,312,442 B1 | 11/2001 | Kieturakis et al. |
| 6,319,265 B1 | 11/2001 | Ginn |
| 6,322,499 B1 | 11/2001 | Evans et al. |
| 6,348,037 B1 | 2/2002 | Chin et al. |
| 6,350,236 B1 | 2/2002 | Hipps et al. |
| 6,361,543 B1 | 3/2002 | Chin et al. |
| 6,387,043 B1 | 5/2002 | Yoon |
| 6,406,425 B1 | 6/2002 | Chin et al. |
| 6,413,208 B1 | 7/2002 | Schollhorn et al. |
| 6,432,044 B1 | 8/2002 | Lunsford et al. |
| 6,432,115 B1 | 8/2002 | Mollenauer et al. |
| 6,433,797 B1 | 8/2002 | Zellweger |
| 6,471,638 B1 | 10/2002 | Chang et al. |
| 6,511,494 B1 | 1/2003 | Knighton et al. |
| 6,520,975 B2 | 2/2003 | Branco |
| 6,527,771 B1 | 3/2003 | Weadock et al. |
| 6,544,260 B1 | 4/2003 | Markel et al. |
| 6,558,313 B1 | 5/2003 | Knighton et al. |
| 6,562,051 B1 | 5/2003 | Bolduc et al. |
| 6,592,582 B2 | 7/2003 | Hess et al. |
| 6,592,604 B2 | 7/2003 | Hess et al. |
| 6,632,227 B2 | 10/2003 | Adams ............... A61B 1/00154 227/180.1 |
| 6,648,898 B1 | 11/2003 | Baxter |
| 6,656,176 B2 | 12/2003 | Hess et al. |
| 6,660,016 B2 | 12/2003 | Lindsay |
| 6,673,087 B1 | 1/2004 | Chang et al. |
| 6,699,180 B2 | 3/2004 | Kobayashi |
| 6,702,813 B1 | 3/2004 | Baxter et al. |
| 6,705,986 B2 | 3/2004 | Fiegel et al. |
| 6,730,020 B2 | 5/2004 | Peng et al. |
| 6,740,102 B2 | 5/2004 | Hess et al. |
| 6,749,609 B1 | 6/2004 | Lunsford et al. |
| 6,752,756 B2 | 6/2004 | Lunsford et al. |
| 6,762,368 B2 | 7/2004 | Saputro et al. |
| 6,811,546 B1 | 11/2004 | Callas et al. |
| 6,814,696 B1 | 11/2004 | Chang et al. |
| 6,814,743 B2 | 11/2004 | Chin et al. |
| 6,830,546 B1 | 12/2004 | Chin et al. |
| 6,863,674 B2 | 3/2005 | Kasahara et al. |
| 6,884,248 B2 | 4/2005 | Bolduc et al. |
| 6,899,670 B2 | 5/2005 | Peng et al. |
| 6,923,759 B2 | 8/2005 | Kasahara et al. |
| 6,951,568 B1 | 10/2005 | Chin |
| 6,963,792 B1 | 11/2005 | Green |
| 6,972,028 B2 | 12/2005 | Chin |
| 6,976,957 B1 | 12/2005 | Chin et al. |
| 7,033,357 B2 | 4/2006 | Baxter et al. |
| 7,066,875 B2 | 6/2006 | Knighton et al. |
| 7,077,803 B2 | 7/2006 | Kasahara et al. |
| 7,097,665 B2 | 8/2006 | Stack et al. |
| 7,146,984 B2 | 12/2006 | Stack et al. |
| 7,211,040 B2 | 5/2007 | Knighton et al. |
| 7,214,180 B2 | 5/2007 | Chin |
| 7,226,409 B2 | 6/2007 | Peng et al. |
| 7,264,587 B2 | 9/2007 | Chin |
| 7,288,096 B2 | 10/2007 | Chin |
| 7,316,683 B2 | 1/2008 | Kasahara et al. |
| 7,326,178 B1 | 2/2008 | Lunsford et al. |
| 7,344,536 B1 | 3/2008 | Lunsford et al. |
| 7,364,657 B2 | 4/2008 | Mandrusov et al. |
| 7,384,423 B1 | 6/2008 | Chin |
| 7,398,781 B1 | 7/2008 | Chin |
| 7,431,725 B2 | 10/2008 | Stack et al. |
| 7,476,198 B1 | 1/2009 | Chin et al. |
| 7,479,104 B2 | 1/2009 | Lau et al. |
| 7,485,092 B1 | 2/2009 | Stewart et al. |
| 7,534,243 B1 | 5/2009 | Chin et al. |
| 7,547,314 B2 | 6/2009 | Kadykowski |
| 7,695,470 B1 | 4/2010 | Stewart et al. |
| 7,733,366 B2 | 6/2010 | Beavers et al. |
| 7,775,970 B2 | 8/2010 | Maeda et al. |
| 7,850,687 B2 | 12/2010 | Kasahara |
| 7,887,558 B2 | 2/2011 | Lin et al. |
| 7,938,842 B1 | 5/2011 | Chin |
| 7,959,553 B2 | 6/2011 | Knighton et al. |
| 7,967,798 B2 | 6/2011 | Reydel et al. |
| 7,972,265 B1 | 7/2011 | Chin et al. |
| 7,981,127 B2 | 7/2011 | Kasahara et al. |
| 7,981,133 B2 | 7/2011 | Chin |
| 8,075,559 B2 | 12/2011 | Stewart et al. |
| 8,465,488 B2 | 6/2013 | Maeda et al. |
| 8,702,700 B2 | 4/2014 | Maeda et al. |
| 8,777,835 B2 | 7/2014 | Knighton et al. |
| 9,700,398 B2 | 7/2017 | Stewart |
| 9,730,782 B2 | 8/2017 | Stewart |
| 10,299,770 B2 * | 5/2019 | Willis ................ A61B 1/018 |
| 2001/0021868 A1 | 9/2001 | Herbst et al. |
| 2002/0026208 A1 | 2/2002 | Roe et al. |
| 2002/0065450 A1 | 5/2002 | Ogawa |
| 2002/0128542 A1 | 9/2002 | Van Over |
| 2002/0169362 A1 | 11/2002 | Kan et al. |
| 2002/0183593 A1 | 12/2002 | Chin et al. |
| 2002/0193850 A1 | 12/2002 | Selman |
| 2003/0032861 A1 | 2/2003 | Lunsford et al. |

(56) References Cited

U.S. PATENT DOCUMENTS

| | | |
|---|---|---|
| 2003/0125719 A1 | 7/2003 | Furnish |
| 2003/0130674 A1 | 7/2003 | Kasahara et al. |
| 2003/0187460 A1 | 10/2003 | Chin et al. |
| 2003/0187461 A1 | 10/2003 | Chin |
| 2003/0236505 A1 | 12/2003 | Bonadio et al. |
| 2003/0236544 A1 | 12/2003 | Lunsford et al. |
| 2004/0097792 A1 | 5/2004 | Moll et al. |
| 2004/0102804 A1 | 5/2004 | Chin |
| 2004/0153098 A1 | 8/2004 | Chin et al. |
| 2004/0153101 A1 | 8/2004 | Bolduc et al. |
| 2004/0181242 A1 | 9/2004 | Stack et al. |
| 2004/0216748 A1 | 11/2004 | Chin |
| 2004/0236231 A1 | 11/2004 | Knighton et al. |
| 2004/0236310 A1 | 11/2004 | Chin et al. |
| 2005/0010242 A1 | 1/2005 | Lindsay |
| 2005/0020911 A1 | 1/2005 | Viswanathan |
| 2005/0065401 A1 | 3/2005 | Saadat et al. |
| 2005/0090709 A1 | 4/2005 | Okada et al. |
| 2005/0124932 A1 | 6/2005 | Foster et al. |
| 2005/0154257 A1 | 7/2005 | Kasahara et al. |
| 2005/0159764 A1 | 7/2005 | Kasahara et al. |
| 2005/0192613 A1 | 9/2005 | Lindsay |
| 2005/0209619 A1 | 9/2005 | Johnson et al. |
| 2005/0247320 A1 | 11/2005 | Stack et al. |
| 2005/0261712 A1 | 11/2005 | Balbierz et al. |
| 2005/0266109 A1 | 12/2005 | Chin et al. |
| 2005/0267499 A1 | 12/2005 | Stack et al. |
| 2005/0283380 A1 | 12/2005 | Garduno |
| 2005/0288622 A1 | 12/2005 | Albrecht et al. |
| 2006/0052660 A1 | 3/2006 | Chin |
| 2006/0074337 A1 | 4/2006 | Yoo |
| 2006/0079915 A1 | 4/2006 | Chin et al. |
| 2006/0094931 A1 | 5/2006 | Danitz et al. |
| 2006/0116746 A1 | 6/2006 | Chin |
| 2006/0149226 A1 | 7/2006 | McCullagh .......... A61B 18/148 606/41 |
| 2006/0206121 A1 | 9/2006 | Chin et al. |
| 2006/0235450 A1 | 10/2006 | Kasahara et al. |
| 2006/0270900 A1 | 11/2006 | Chin et al. |
| 2006/0271032 A1 | 11/2006 | Chin et al. |
| 2006/0287574 A1 | 12/2006 | Chin |
| 2006/0287734 A1 | 12/2006 | Stack et al. |
| 2007/0060932 A1 | 3/2007 | Stack et al. |
| 2007/0118206 A1 | 5/2007 | Colgan et al. |
| 2007/0123799 A1 | 5/2007 | Meireles |
| 2007/0162067 A1 | 7/2007 | Lunsford et al. |
| 2007/0167692 A1 | 7/2007 | Kim |
| 2007/0198043 A1 | 8/2007 | Cox et al. |
| 2007/0219571 A1 | 9/2007 | Balbierz et al. |
| 2007/0238917 A1 | 10/2007 | Peng et al. |
| 2007/0260273 A1 | 11/2007 | Cropper et al. |
| 2007/0276432 A1 | 11/2007 | Stack et al. |
| 2008/0039879 A1 | 2/2008 | Chin et al. |
| 2008/0065122 A1 | 3/2008 | Stack et al. |
| 2008/0097523 A1 | 4/2008 | Bolduc et al. |
| 2008/0103365 A1 | 5/2008 | Lunsford et al. |
| 2008/0132892 A1 | 6/2008 | Lunford et al. |
| 2008/0145345 A1 | 6/2008 | Mandrusov et al. |
| 2008/0145469 A1 | 6/2008 | Chin et al. |
| 2008/0208191 A1 | 8/2008 | Kadykowski |
| 2008/0255589 A1 | 10/2008 | Blakeney et al. |
| 2008/0306333 A1 | 12/2008 | Chin |
| 2008/0306335 A1 | 12/2008 | Lau et al. |
| 2009/0023986 A1 | 1/2009 | Stewart |
| 2009/0024156 A1 | 1/2009 | Chin |
| 2009/0062610 A1 | 3/2009 | Williams |
| 2009/0112122 A1 | 4/2009 | Chuang |
| 2009/0281388 A1 | 11/2009 | Ito |
| 2009/0322513 A1 | 12/2009 | Hwang |
| 2009/0326372 A1 | 12/2009 | Darlington |
| 2010/0234843 A1 | 9/2010 | Stewart |
| 2010/0292533 A1 | 11/2010 | Kasahara et al. |
| 2011/0202082 A1 | 8/2011 | Chin |
| 2012/0078037 A1 | 3/2012 | Stewart |
| 2013/0211197 A1 | 8/2013 | Kano et al. |
| 2017/0332893 A1 | 11/2017 | Irion et al. |

FOREIGN PATENT DOCUMENTS

| | | |
|---|---|---|
| AU | 199942354 A1 | 7/1999 |
| AU | 199935034 A1 | 1/2000 |
| AU | 199942354 A1 | 3/2000 |
| AU | 719712 B2 | 5/2000 |
| AU | 199935034 A1 | 6/2000 |
| AU | 2002227086 B2 | 5/2002 |
| AU | 2007203086 A1 | 1/2009 |
| CA | 2244164 A1 | 7/1997 |
| CA | 2274270 A1 | 12/1999 |
| CA | 2279661 A1 | 2/2000 |
| CA | 2427918 A1 | 5/2002 |
| CA | 2592766 A1 | 12/2008 |
| DE | 24699 | 5/1883 |
| DE | 40469 C | 10/1886 |
| DE | H24669 | 10/1956 |
| DE | 2415263 A1 | 10/1975 |
| DE | 2550693 A1 | 5/1977 |
| DE | 3002088 A1 | 7/1981 |
| DE | 3525917 A1 | 2/1986 |
| DE | 3942589 A1 | 7/1991 |
| DE | 19906260 A1 | 9/1999 |
| DE | 19827360 A1 | 1/2000 |
| EP | 131347 A2 | 1/1985 |
| EP | 0131347 A2 | 1/1985 |
| EP | 0131347 A3 | 1/1985 |
| EP | 131347 A3 | 3/1986 |
| EP | 0243714 A2 | 11/1987 |
| EP | 0341943 A2 | 11/1989 |
| EP | 341943 A2 | 11/1989 |
| EP | 0409569 A1 | 1/1991 |
| EP | 409569 A1 | 1/1991 |
| EP | 0517244 B1 | 9/1992 |
| EP | 0517244 A1 | 12/1992 |
| EP | 517244 A1 | 12/1992 |
| EP | 518230 A1 | 12/1992 |
| EP | 0518230 A1 | 12/1992 |
| EP | 0518230 B1 | 12/1992 |
| EP | 0645244 A1 | 3/1995 |
| EP | 664104 A2 | 7/1995 |
| EP | 0664104 A2 | 7/1995 |
| EP | 0681811 A2 | 11/1995 |
| EP | 681811 A2 | 11/1995 |
| EP | 517244 B1 | 3/1996 |
| EP | 518230 B1 | 5/1996 |
| EP | 761171 A2 | 3/1997 |
| EP | 0761171 A2 | 3/1997 |
| EP | 0769270 A1 | 4/1997 |
| EP | 769270 A1 | 4/1997 |
| EP | 0845244 A1 | 6/1998 |
| EP | 0867148 A1 | 9/1998 |
| EP | 867148 A1 | 9/1998 |
| EP | 878168 A1 | 11/1998 |
| EP | 0878168 A1 | 11/1998 |
| EP | 0979635 A2 | 2/2000 |
| EP | 0980673 A2 | 2/2000 |
| EP | 1339352 A2 | 9/2003 |
| EP | 0761171 B1 | 3/2005 |
| EP | 761171 B1 | 3/2005 |
| FR | 2265344 A1 | 10/1975 |
| FR | 2265344 B3 | 12/1977 |
| GB | 2082459 A | 3/1982 |
| GB | 2195540 A | 4/1988 |
| JP | 727043 A | 1/1995 |
| JP | 7027043 A | 1/1995 |
| JP | 2802244 A | 7/1998 |
| JP | 2802244 B2 | 10/1998 |
| JP | 11172954 A | 6/1999 |
| JP | 11225282 A | 8/1999 |
| JP | 200037389 A | 2/2000 |
| JP | 200051221 A | 2/2000 |
| JP | 2000037389 A | 2/2000 |
| JP | 2000051221 A2 | 2/2000 |
| JP | 2007509702 A | 4/2007 |

(56) References Cited

FOREIGN PATENT DOCUMENTS

| | | | |
|---|---|---|---|
| JP | 2007509702 T | 4/2007 |
| JP | 2007175478 A | 7/2007 |
| SU | 112367 A1 | 11/1957 |
| SU | 510235 A1 | 4/1976 |
| SU | 639545 A1 | 12/1978 |
| SU | 1371689 A1 | 2/1988 |
| SU | 1498474 A1 | 8/1989 |
| WO | 9108710 A1 | 6/1991 |
| WO | 1991008710 A1 | 6/1991 |
| WO | 9208513 A1 | 5/1992 |
| WO | 1992008513 A1 | 5/1992 |
| WO | 9220291 A1 | 11/1992 |
| WO | 1992020291 A1 | 11/1992 |
| WO | 9308754 A1 | 5/1993 |
| WO | 1993008754 A1 | 5/1993 |
| WO | 9418881 A1 | 9/1994 |
| WO | 1994018881 A1 | 9/1994 |
| WO | 9424949 A1 | 11/1994 |
| WO | 9424951 A1 | 11/1994 |
| WO | 1994024949 A1 | 11/1994 |
| WO | 1994024951 A1 | 11/1994 |
| WO | 9510982 A1 | 4/1995 |
| WO | 1995010982 A1 | 4/1995 |
| WO | 9519737 A1 | 7/1995 |
| WO | 1995019737 A1 | 7/1995 |
| WO | 9601130 A1 | 1/1996 |
| WO | 1996001130 A1 | 1/1996 |
| WO | 9630072 A1 | 10/1996 |
| WO | 1996030072 A1 | 10/1996 |
| WO | 9636287 A1 | 11/1996 |
| WO | 9716125 A1 | 5/1997 |
| WO | 1997016125 A1 | 5/1997 |
| WO | 9726831 A1 | 7/1997 |
| WO | 1997026831 A1 | 7/1997 |
| WO | 9733522 A1 | 9/1997 |
| WO | 1997033522 A1 | 9/1997 |
| WO | 9737701 A1 | 10/1997 |
| WO | 1997037701 A1 | 10/1997 |
| WO | 9802084 A2 | 1/1998 |
| WO | 9802102 A2 | 1/1998 |
| WO | 9802102 A3 | 1/1998 |
| WO | 1998002084 A2 | 1/1998 |
| WO | 1998002102 A2 | 1/1998 |
| WO | 9806451 A1 | 2/1998 |
| WO | 1998006451 A1 | 2/1998 |
| WO | 1998002102 A3 | 3/1998 |
| WO | 9838935 A | 9/1998 |
| WO | 1998038935 A1 | 9/1998 |
| WO | 9964109 A1 | 12/1999 |
| WO | 0040139 A1 | 7/2000 |
| WO | 0040160 A2 | 7/2000 |
| WO | 2000040139 A1 | 7/2000 |
| WO | 2000040160 A2 | 7/2000 |
| WO | 0239882 A2 | 5/2002 |
| WO | 03057062 A2 | 7/2003 |
| WO | 2003057062 A2 | 7/2003 |
| WO | 03094758 A1 | 11/2003 |
| WO | 2003094758 A1 | 11/2003 |
| WO | 03105706 A1 | 12/2003 |
| WO | 2003105706 A1 | 12/2003 |
| WO | 2004066828 A2 | 8/2004 |
| WO | 2004066829 A2 | 8/2004 |
| WO | 2004073506 A2 | 9/2004 |
| WO | 2005006955 A2 | 1/2005 |
| WO | 2005044079 A2 | 5/2005 |
| WO | 2009036287 A1 | 3/2009 |

OTHER PUBLICATIONS

Non-Final Office Action issued in U.S. Appl. No. 15/686,103, dated Dec. 27, 2018.
Webster's II New College Dictionary, 1995, 59, Houghton Mifflin Company, Boston, MA.
Filter Selection Guide (Waco), at http://www.wacofilters.com/WACO/Admin/Uploads/Documents/Filter%20Selection%20Guide.pdf (downloaded Feb. 19, 2015), 2 pages.
European Search Report for EP Application No. 07013134.7-1526, dated Jan. 17, 2008, pp. 1-6.
Products for Precision—Focused Clinicians, [online], [Retrieved on Feb. 13, 2008, Copyright 2008], Retrieved from URL: http://www.terumo-cvs.com/products/.
Office Action issued in U.S. Appl. No. 11/446,024 dated Oct. 23, 2009. (12 pages).
Office Action issued in U.S. Appl. No. 11/446,024 dated Apr. 26, 2010. (13 pages).
Final Office Action issued in U.S. Appl. No. 11/446,024 dated Aug. 26, 2010. (18 pages).
Office Action issued in U.S. Appl. No. 11/446,024 dated Apr. 4, 2014. (22 pages).
Final Office Action issued in U.S. Appl. No. 11/446,024 dated Nov. 20, 2014. (28 pages).
Office Action issued in U.S. Appl. No. 11/446,024 dated Oct. 8, 2015. (15 pages).
Final Office Action issued in U.S. Appl. No. 11/446,024 dated Jul. 13, 2016. (15 pages).
Office Action issued in U.S. Appl. No. 11/446,024 dated Nov. 16, 2016. (15 pages).
Final Office Action issued in U.S. Appl. No. 11/446,024 dated Mar. 7, 2017. (17 pages).
Office Action issued in U.S. Appl. No. 15/686,046 dated Nov. 8, 2017. (10 pages).
Final Office Action issued in U.S. Appl. No. 15/686,046 dated Mar. 30, 2018. (11 pages).
Final Office Action issued in U.S. Appl. No. 15/686,103 dated Apr. 11, 2019. (15 pages).
Final Office Action issued in U.S. Appl. No. 15/686,703 dated May 30, 2019. (9 pages).
Office Action issued in U.S. Appl. No. 15/686,703 dated Jan. 25, 2021. (6 pages).
Office Action issued in U.S. Appl. No. 16/552,963 dated Apr. 15, 2021. (8 pages).
Extended European Search Report issued in EP Application No. 07013134.7 dated Apr. 7, 2008. (11 pages).
Illig, Karl A. et al., Financial Impact of Endoscopic Vein Harvest for Infrainguinal Bypass, Journal of Vascular Surgery, 37, 2, 2003, 323-330, plus appendix.

* cited by examiner

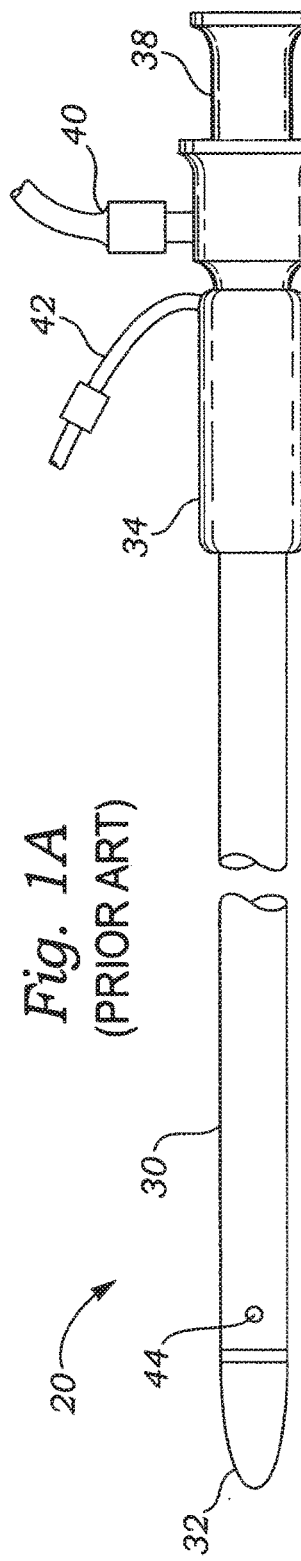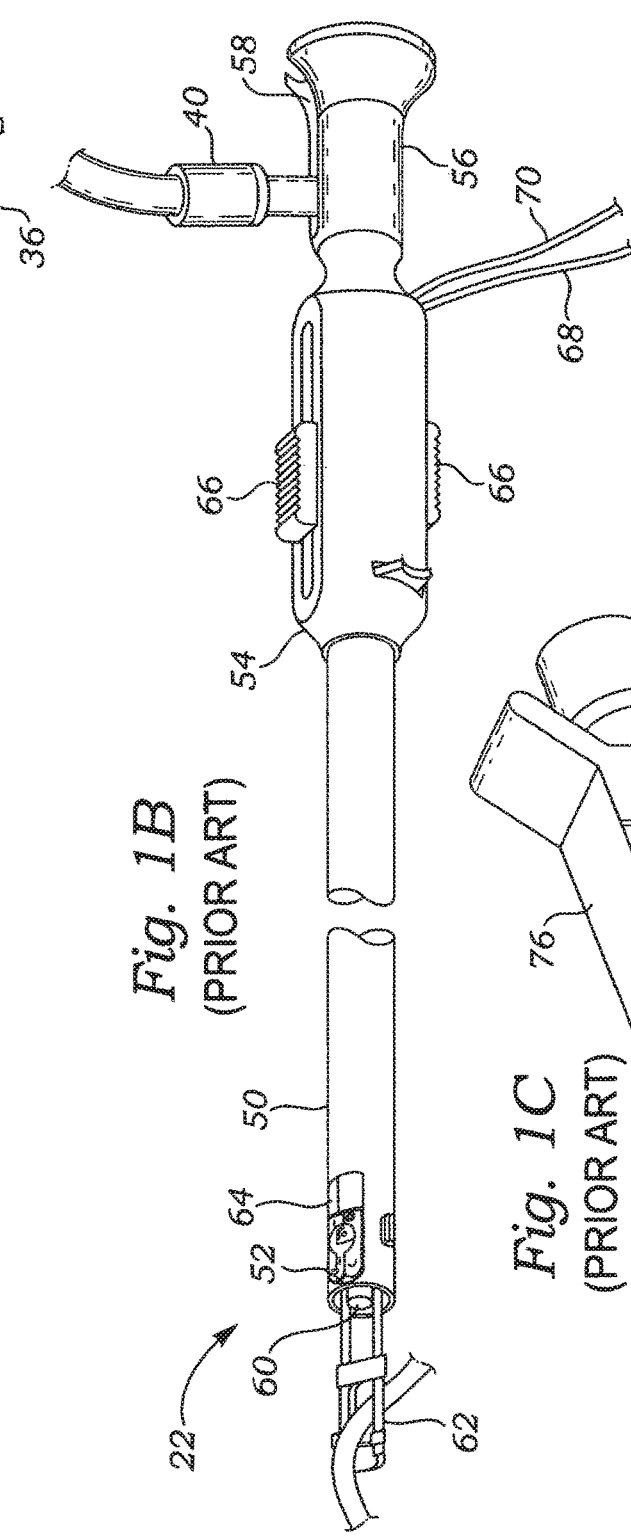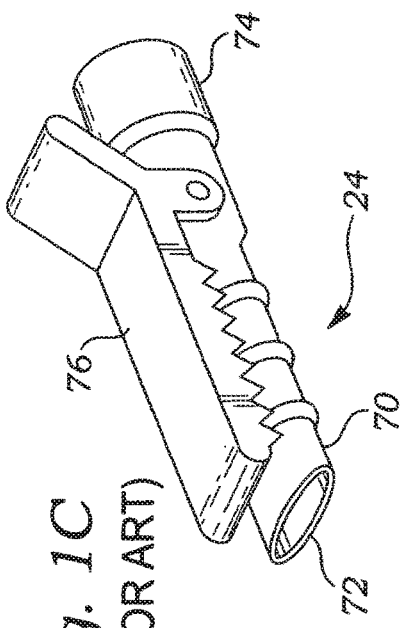
Fig. 1A (PRIOR ART)
Fig. 1B (PRIOR ART)
Fig. 1C (PRIOR ART)

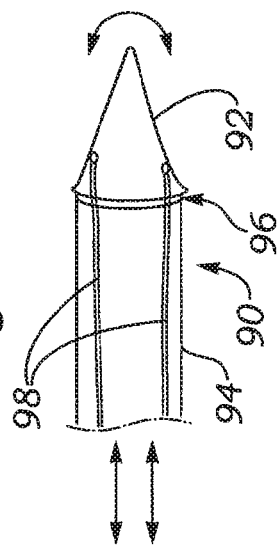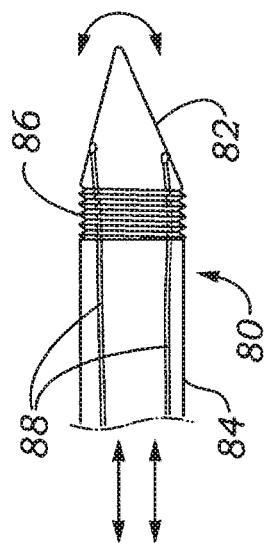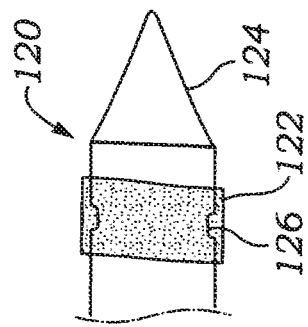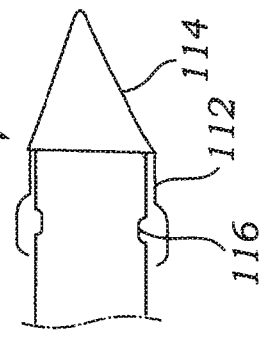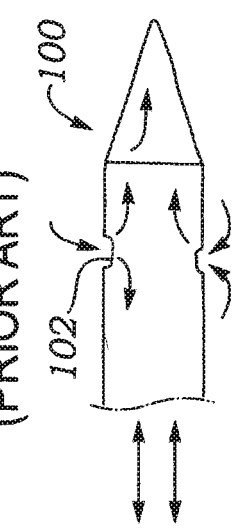

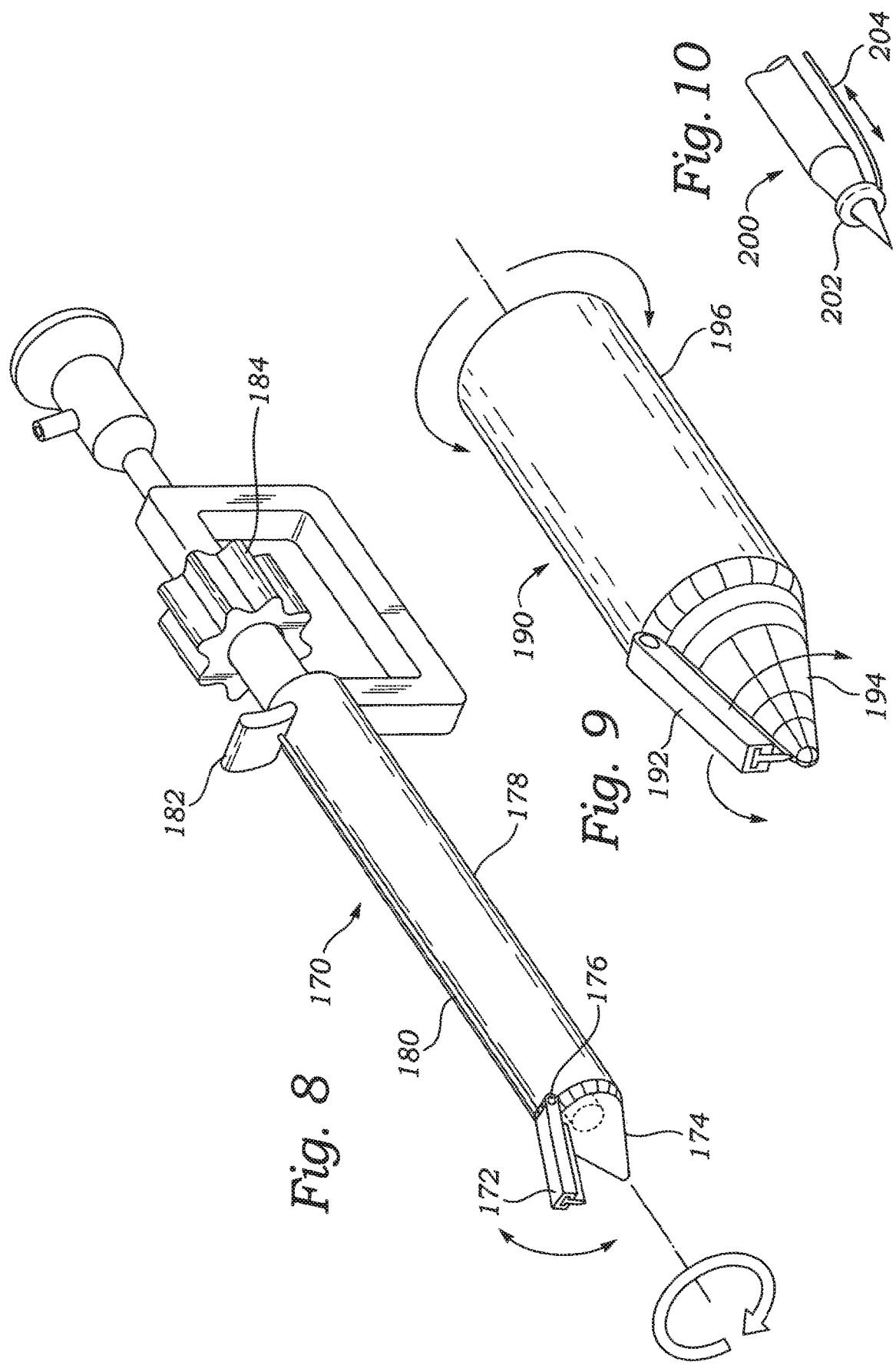

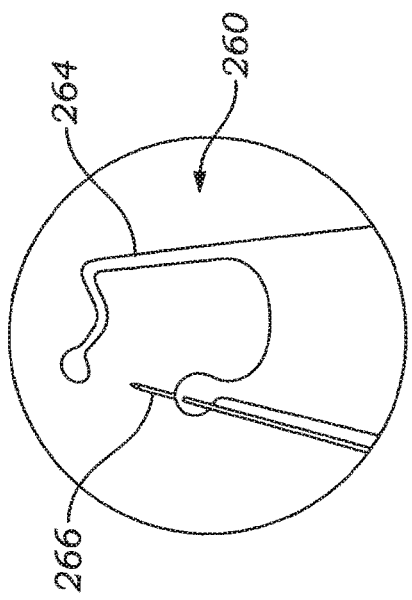
Fig. 16A
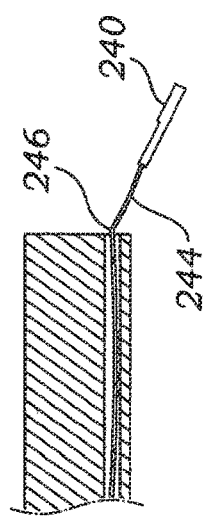
Fig. 16B
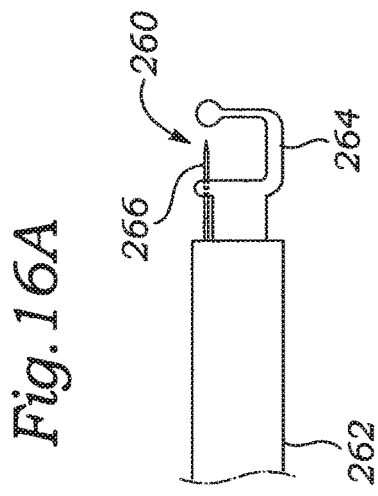
Fig. 15A
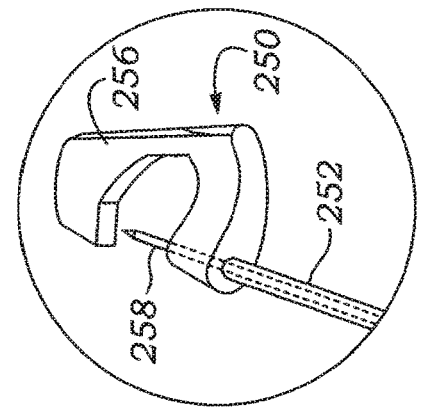
Fig. 15B
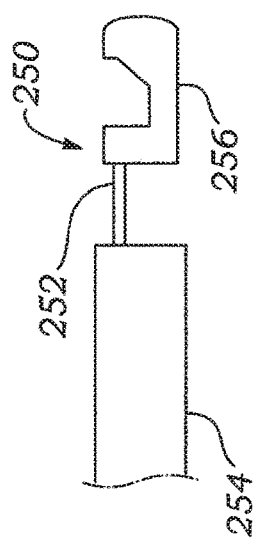
Fig. 14A
Fig. 14B
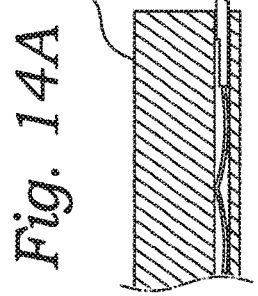
Fig. 14C

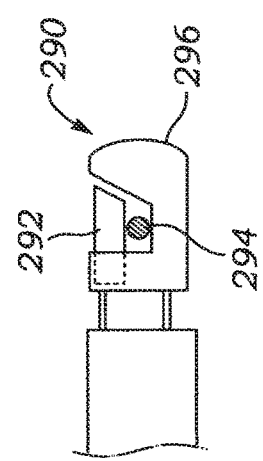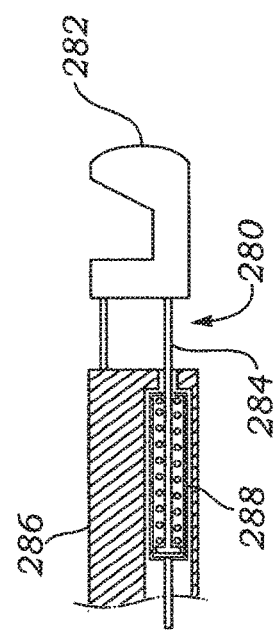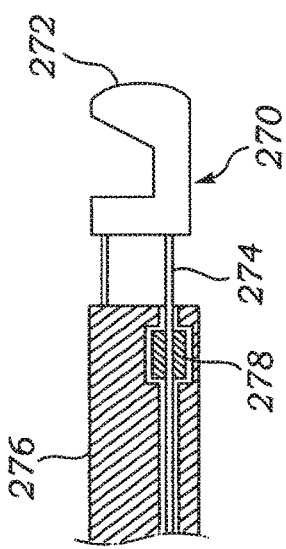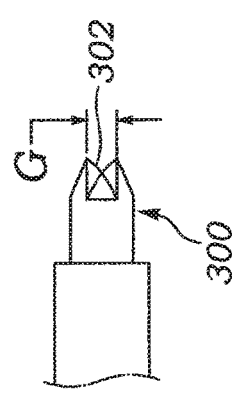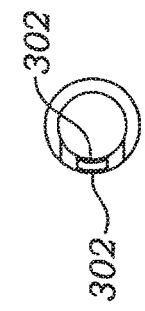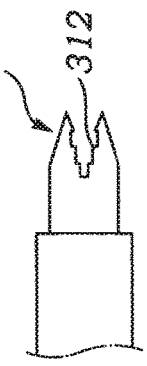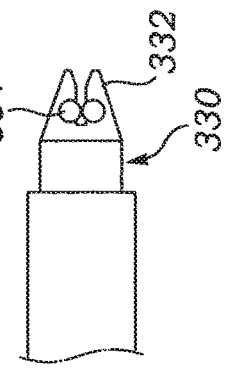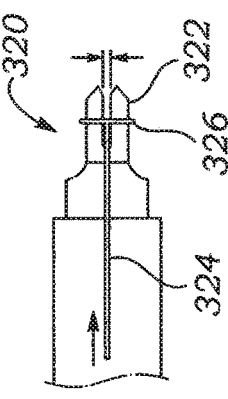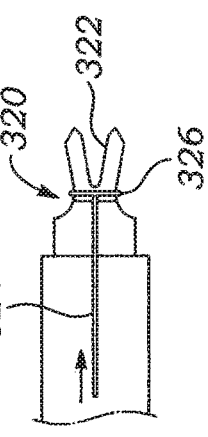

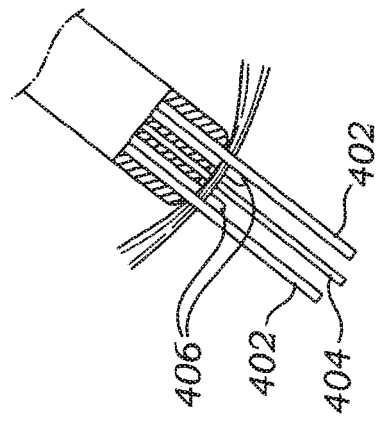
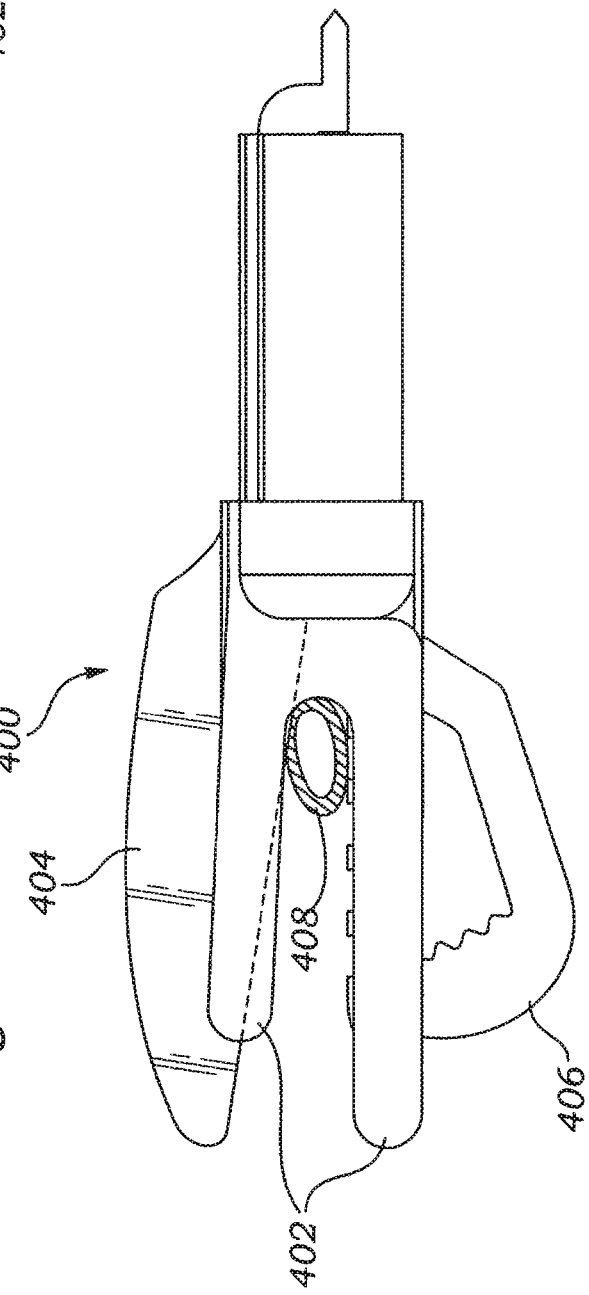

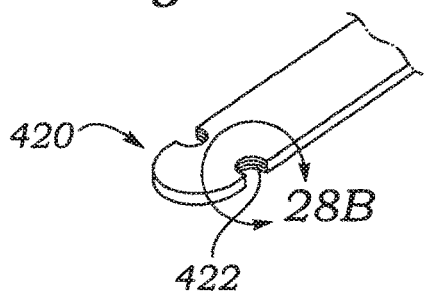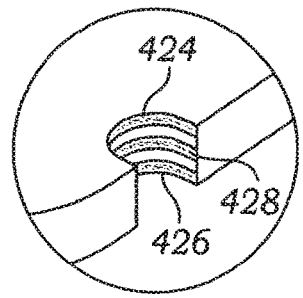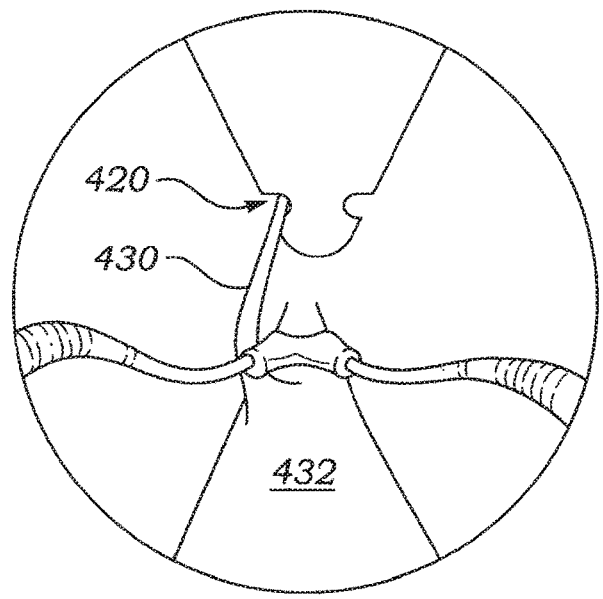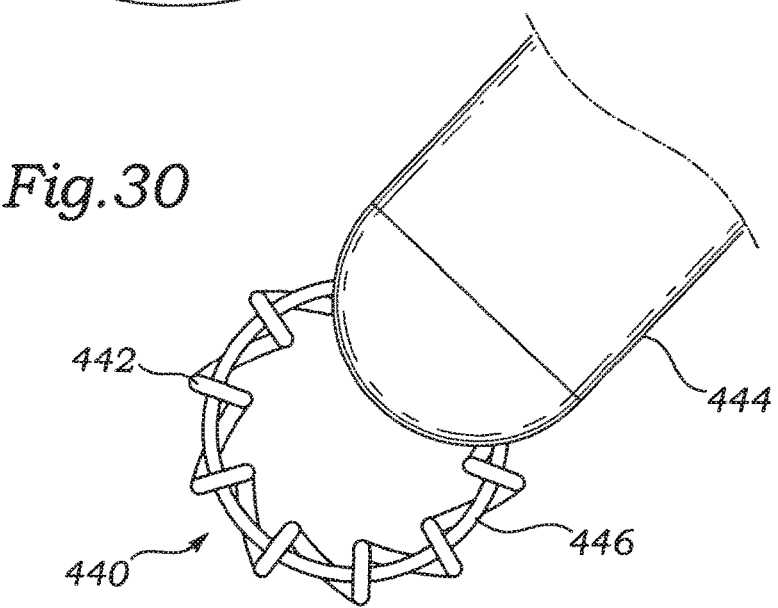

ENDOSCOPIC VESSEL HARVESTING SYSTEM COMPONENTS

This application is a divisional application of U.S. patent application Ser. No. 15/686,046 (now U.S. Pat. No. 10,299,770 B2) filed on Aug. 24, 2017, which is a divisional application of U.S. patent application Ser. No. 11/446,024 (now U.S. Pat. No. 9,770,230 B2), which was filed on Jun. 1, 2006. The above-mentioned applications and patents are incorporated herein by reference in their entirety.

FIELD OF THE INVENTION

The present invention relates to surgical devices and methods for dissection and removal of blood vessels from a patient's body and, in particular, to endoscopic vessel harvesting systems, components and methods.

BACKGROUND OF THE INVENTION

Endoscopic harvesting of vessels is well known in the surgical field and has been the subject of a great deal of recent technological advancement. Typically, the harvested vessel is used for bypass or as a shunt around an artery that has diminished flow from stenosis or other anomaly, such as in a Coronary Artery Bypass Grafting (CABG) procedure. Often in CABG, a saphenous vein from the patient's leg is harvested for subsequent use in the surgery. Other vessels, such as the radial artery, can also be harvested and used in this manner. Vessel harvesting involves liberating the vessel from surrounding tissue and transecting smaller side branches, cauterizing, tying or ligating the vessel at a proximal site and a distal site, and then transecting the vessel at both sites before it is removed from the body.

Known endoscopic methods and devices for performing vessel harvesting are discussed in detail in U.S. Pat. No. 6,176,825 to Chin, et al., Re 36,043 to Knighton, U.S. Pat. No. 6,406,425 to Chin, et al., and U.S. Pat. No. 6,471,638 to Chang, et al., all of which are expressly incorporated herein by reference. Furthermore, various devices and methods disclosed in U.S. Pat. No. 5,895,353 to Lunsford, et al., and U.S. Pat. No. 6,162,173 to Chin, et al., and pending patent application Ser. No. 10/602,490 entitled "Apparatus and Method for Integrated Vessel Ligator and Transector" are also expressly incorporated herein by reference. Also, commercial vessel harvesting systems sold under the tradename VASOVIEW® Uniport Plus, VASOVIEW® 5, VASOVIEW® 6, and VASOVIEW® 7 are available from Guidant Corporation of Santa Clara, Calif.

Another version of an endoscopic vessel harvesting system is disclosed in U.S. Patent Publication No. 2003/0130674 to Kasahara, et al., filed on Dec. 24, 2002, or and later updated in U.S. Patent Publication No. 2005/0159764 also to Kasahara, et al., filed Oct. 27, 2004. In these systems, various devices are utilized to first dissect a vein from surrounding tissue and then harvest the vein. Each of the devices passes through a guide tube of a trocar inserted through a body surface, such as disclosed in U.S. Pat. No. 6,863,674 also to Kasahara, et al., filed Dec. 23, 2002. Certain elements of these and other related patent disclosures are evident in the VirtuoSaph™ endoscopic vein harvesting system (see, www.terumo-cvs.com/products) marketed by Terumo Cardiovascular Systems Corp. of Japan.

Despite accepted endoscopic vessel harvesting systems and techniques, there remains a need for systems and components that both make the user's task less complicated and improve the surgical outcome.

SUMMARY OF THE INVENTION

The present invention provides an endoscopic vessel harvesting system suitable for harvesting various target vessels that allows for simple and convenient operation in a limited space. The invention includes improvements to various components of vessel harvesting systems each of which can be used with any of the other component improvements. It should be understood, therefore, that even if a particular combination is not explicitly described, any one component can be used with any other component disclosed herein unless that combination is structurally impossible.

In accordance with a first embodiment, the present invention provides a vessel dissector that is used in conjunction with an endoscope, comprising an elongated cannula including a lumen therein for receiving the endoscope, the elongated cannula further housing a passage for delivery of an insufflation gas therethrough. The vessel dissector has an input for connecting to a supply of insufflation gas, the input being in fluid communication with the passage. A port opens near the distal end of the elongated cannula in fluid communication with the passage and out of which insufflation gas is expelled. A fluid barrier covers the port that permits expulsion of insufflation gas from the passage within the elongated cannula and prevents ingress of fluid from outside the elongated cannula through the port to the passage.

The port may be formed in the side of the elongated cannula. Desirably, the fluid barrier comprises a tubular member surrounding the distal end of the elongated cannula and covering the port. In one embodiment, the fluid barrier comprises a polymer shield that closes off the port from the outside but is flexible so that insufflation gas may escape from the passage therethrough. In another embodiment, the fluid barrier comprises a gas-permeable liquid-resistant membrane that permits escape of insufflation gas therethrough but prevents entrance of fluid to the passage.

The vessel dissector may further include a transparent conical tip on a distal end of the elongated cannula that permits an operator of the dissector to dissect tissue while viewing internal body structures via an objective lens of the endoscope positioned close to the blunt tip. The insufflation gas port may be located at the apex of the conical tip. The vessel dissector may also have a coupling between the distal end of the elongated cannula and the transparent blunt tip and a control member extending through the elongated cannula to enable the user to angle the tip relative to the axis of the elongated cannula. For instance, the coupling may be an accordion-like flexible interface or sleeve, or a spherical bearing surface, In accordance with a second embodiment, the present invention provides a vessel dissector that is used in conjunction with an endoscope, comprising an elongated cannula including a lumen therein for receiving the endoscope. A hollow outwardly conical transparent dissecting tip on a distal end of the elongated cannula permits an operator of the dissector to dissect tissue while viewing internal body structures via an objective lens of the endoscope. The tip comprises a structure generally arranged about an axis and having an inner wall that terminates at a distal end in a shape that tends to reduce glare back to the objective lens of the endoscope in comparison to a conical inner wall that tapers symmetrically to an apex. For example, the shape of the distal end of the inner wall of the dissecting tip may be an inner tapering surface that terminates at its distal end in a line so as to form an elongated inner corner, an inner surface that tapers downward toward its distal end and terminates in a flat surface set at an angle from the axis of the tip, or a backward wedge. Desirably, the dissecting tip has a tip diameter and the elongated cannula has a diameter adjacent the dissecting tip that is between about 50-75% of the tip diameter.

In a more robust system, the vessel dissector may also include a vessel holding tool extending through the elongated cannula and adapted for longitudinal movement therein, and a vessel severing tool such as a tissue welder extending through the elongated cannula and adapted for longitudinal movement therein. In this embodiment, the dissecting tip includes apertures for passage of the vessel holding tool and the vessel severing tool. Preferably, both the vessel holding tool and the vessel severing tool dock into recesses in the dissecting tip and have exterior shapes that conform to the conical exterior of the dissecting tip so as to match its shape.

In accordance with a third embodiment, the present invention provides a vessel dissector that is used in conjunction with an endoscope. The vessel dissector is defined by an elongated cannula including a lumen therein for receiving the endoscope. A transparent blunt tip on a distal end of the elongated cannula permits an operator of the dissector to dissect tissue while viewing internal body structures via an objective lens of the endoscope. A wiper clears tissue from the exterior of the transparent blunt tip. The wiper may be arranged on the elongated cannula to pivot about an axis to alternately contact and disengage from the transparent blunt tip, and a mechanism for rotating the blunt tip. Alternatively, the wiper is arranged on the elongated cannula to contact the blunt tip and swivel about the axis of the device. Still further, the wiper may be an O-ring wiper fitted over the blunt tip and connected to an actuation rod that displaces the O-ring wiper longitudinally to wipe over the blunt tip. In one embodiment, the wiper is arranged on the elongated cannula to contact the blunt tip and has an energized cutting electrode thereon to remove tissue via ablation. Preferably, a handle disposed at a proximal end of the elongated cannula has a thumb lever thereon connected to an actuating rod for displacing the wiper relative to the transparent blunt tip and clearing tissue therefrom.

In accordance with a fourth embodiment, a vessel harvester used in conjunction with an endoscope comprises an elongated cannula including a lumen therein for receiving the endoscope, and a vessel holding tool extending through the elongated cannula and adapted for longitudinal movement therein. A distal end of the vessel holding tool includes a vessel hook and a locking member used to capture a target vessel, wherein the hook is open on one side and extension of the locking member closes the open side so that the target vessel is completely surrounded and captured therein. A vessel severing tool extends through the elongated cannula for longitudinal movement therein, and has a distal operative end with structure for severing a target vessel. The vessel holding tool includes a support rod that extends through the elongated cannula and which is configured to angle laterally at a location close to the distal end of the tool to enable lateral vessel manipulation and improve positioning of the vessel severing tool relative to the target vessel.

Desirably, the support rod is bent out of a plane in which the support rod lies at a location close to the distal end of the vessel holding tool such that the distal end angles either toward or away from the vessel severing tool. The support rod may be flexible such that the bend is retracted into the cannula and distal extension of the vessel holding tool from the end of the elongated cannula displaces its distal end laterally. A flexible support rod may be surrounded by a rigid hypotube also adapted for longitudinal movement with respect to the cannula, wherein extension of both the support rod and hypotube from the cannula and then retraction of the hypotube from around the support rod angles the vessel holding tool. Alternatively, the support rod is bent out of a plane in which the support rod lies at a location close to the distal end of the vessel holding tool using an active angling mechanism controlled from a proximal end of the elongated cannula.

The vessel hook of the vessel holding tool may include a blunt tapered distal dissecting surface for blunt dissection of tissue. Further, the vessel hook of the vessel holding tool defines a space therein for receiving a target vessel, and the locking member may be shaped as a large wedge to reduce the space within the open vessel hook by about 50% and includes a tapered leading edge that helps prevent pinching of the target vessel as the locking member extends.

In accordance with a fifth embodiment, the present invention provides a vessel harvester that is used in conjunction with an endoscope, comprising an elongated cannula including a lumen therein for receiving the endoscope. A vessel severing tool extends through the elongated cannula for longitudinal movement therein, the severing tool having a distal operative end with structure for severing a target vessel. A vessel holding tool also extends through the elongated cannula for longitudinal movement therein and has a single support rod that extends through the elongated cannula and a distal end with a vessel hook and a locking member used to capture a target vessel and manipulate it to present a side branch of the target vessel to the vessel severing tool. The hook is open on one side and extension of the locking member closes the open side so that the target vessel is completely surrounded and captured therein. The locking member extends concentrically from the single support rod on one lateral side of the vessel hook, the single support rod therefore reducing endoscopic viewing impediments relative to more than one support rod.

The support rod may be configured to angle laterally at a location close to the distal end of the tool to enable lateral vessel manipulation and improved positioning of the vessel severing tool relative to the target vessel. Desirably, the vessel hook of the vessel holding tool includes a blunt tapered distal dissecting surface for blunt dissection of tissue.

In accordance with a sixth embodiment, the present invention provides a vessel harvester that is used in conjunction with an endoscope, comprising an elongated cannula including a lumen therein for receiving the endoscope. A vessel severing tool extends through the elongated cannula for longitudinal movement therein, the severing tool having a distal operative end with structure for severing a target vessel. A vessel holding tool also extends through the elongated cannula for longitudinal movement therein. The vessel holding tool has a support rod that extends through the elongated cannula and a distal end with a vessel hook and a locking member used to capture a target vessel and manipulate it to present a side branch of the target vessel to the vessel severing tool. The hook is open on one side and extension of the locking member closes the open side so that the target vessel is completely surrounded and captured therein. The distal end of the vessel holding tool including the hook and locking member are constructed of a thin wireform for reduced impediment to endoscopic viewing. Preferably, the thin wireform is formed of metal or plastic wires having a thickness of between about 0.5 mm and 1.0 mm. Desirably, the support rod is configured to angle laterally at a location close to the distal end of the tool to enable lateral vessel manipulation and improved positioning of the vessel severing tool relative to the target vessel, In accordance with a seventh embodiment, the present invention provides a vessel harvester that is used in conjunction with an endoscope, comprising an elongated cannula including a lumen therein for receiving the endoscope. A vessel severing tool extends through the elongated cannula for longitudinal movement therein, the severing tool having a distal operative end with structure for severing a target vessel. A vessel holding tool also extends through the elongated cannula for longitudinal movement therein. The vessel holding tool has a support rod that extends through the elongated cannula and a distal end with a vessel holder used to capture a target vessel and manipulate it to present a side branch of the target vessel to the vessel severing tool. A damped slip mechanism provided around the support rod of the vessel holding tool permits relative movement between the cannula and the support rod if the vessel holder catches on any body structure and generates a reaction force in the support rod in opposition to movement of the cannula. For instance, the damped slip mechanism comprises a friction collar surrounding the support rod, or a piston/cylinder/spring arrangement that couples movement of the support rod and cannula.

In a preferred embodiment wherein the vessel holder of the vessel holding tool is open on one side and defines a space therein for receiving a target vessel. A locking member moves to close the open side of the holder so that the target vessel is completely surrounded and captured therein. The locking member is shaped as a large wedge to reduce the space within the open vessel holder by about 50% and includes a tapered leading edge that helps prevent pinching of the target vessel as the locking member moves. Also, the vessel holding tool has improved visibility by virtue of a single support rod that extends through the elongated cannula, wherein the locking member extends concentrically from the single support rod on one lateral side of the vessel holder, the single support rod therefore reducing endoscopic viewing impediments relative to more than one support rod. Desirably, the distal end of the vessel holding tool including the holder and locking member are constructed of a thin wireform for reduced impediment to endoscopic viewing.

In accordance with an eighth embodiment, the present invention provides a vessel harvester that is used in conjunction with an endoscope, comprising an elongated cannula including a lumen therein for receiving the endoscope. A vessel severing tool extends through the elongated cannula for longitudinal movement therein, the severing tool has a distal operative end with an open mouth for receiving a target vessel that automatically accommodates widely varying sizes of vessel, and a severing device associated with the mouth. A vessel holding tool extends through the elongated cannula for longitudinal movement therein, the vessel holding tool having structure used to capture a target vessel and manipulate it to relative to the vessel severing tool. The mouth of the vessel severing tool preferably accommodates vessels having diameters that range from between 0.5 and 1.0 mm.

In one embodiment, the mouth has facing vessel contacts that flex apart upon receiving a vessel therebetween. The severing device may have bipolar electrodes disposed to contact a target vessel received within the mouth. For instance, the bipolar electrodes comprise wire electrodes arranged in a crossing pattern in the mouth. In another version, the mouth has a stepped shape with several progressively smaller intermediate gaps having generally parallel sides that provide regions of constant width surface contact with the vessel. The intermediate gaps may have widths in decreasing increments of 1.0 mm. The severing device may be a mechanical cutter disposed transverse to a target vessel received within the mouth. For efficacy, a fluid conduit terminates close to the distal operative end of the vessel severing tool and is adapted to deliver a fluid jet to knock away tissue that may stick to the distal operative end.

The vessel severing tool may be connected to a control rod and located within an arcuate slot formed in the elongated cannula, the control rod being capable of translating the distal operative end laterally within the arcuate slot as well as longitudinally. The mouth of the vessel severing tool may open to one side of the distal operative end. The vessel holding tool may includes a support rod that extends through the elongated cannula and is bent out of a plane in which the support rod lies at a location close to the distal end of the vessel holding tool such that the distal end angles either toward or away from the vessel severing tool.

In accordance with a ninth embodiment, the present invention provides a vessel harvester that is used in conjunction with an endoscope, comprising an elongated cannula including a lumen therein for receiving the endoscope. A pair of partial tubular vessel shields extend from the cannula and define a lumen sized to receive a target vessel, the partial tubular vessel shields defining gaps therebetween sized to receive a side branch extending from the target vessel. A tubular cutting element sized to surround the partial tubular vessel shields and axially displaceable from the cannula, advances to sever any side branch received within the gaps while the partial tubular vessel shields protect the target vessel from the severing operation. The vessel severing tool may be a tubular knife blade. A fluid conduit terminating close to the partial tubular vessel shields may be adapted to deliver a fluid jet to knock away tissue that may stick to the vessel shields.

In accordance with a tenth embodiment, the present invention provides a vessel harvester that is used in conjunction with an endoscope, comprising an elongated cannula including a lumen therein for receiving the endoscope. A pair of fork-shaped vessel sealing electrodes having tines are spaced laterally apart so as to create a gap therebetween. A vessel capturing mandible moves within the gap between the electrodes to capture a target vessel positioned between the tines. A severing blade moves within the gap and sever the target vessel. Desirably, the vessel capturing mandible has a serrated distal finger to securely capture the target vessel within the tines. Both of the vessel capturing mandible and severing blade may have control rods and angled proximal surfaces that cam against a distal end of the elongated cannula and displace them toward one another upon proximal retraction of the control rods. A fluid conduit terminating close to the fork-shaped vessel sealing electrodes may deliver a fluid jet to knock away tissue that sticks to the sealing electrodes.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIG. 2A is a perspective view of an endoscopic vessel dissector of the prior art;

FIG. 1B is a perspective view of an endoscopic vessel harvester of the prior art;

FIG. 1C is a perspective view of an access trocar of the prior art;

FIGS. 2A and 2B are side views of the distal end of alternative vessel dissectors of the present invention including articulated dissecting tips;

FIG. 3 is a side view schematically illustrating the possible path of bodily fluids into the prior art endoscopic vessel dissector of FIG. 1A;

FIGS. 4A and 4B are side views of the distal end of alternative vessel dissectors of the present invention including structures for inhibiting ingress of bodily fluids into the dissector cannula;

FIG. 8 is a perspective view of an endoscopic vessel dissector of the present invention having a wiper blade for clearing the distal tip;

FIGS. 9 and 10 are perspective views of the distal tip of two alternative endoscopic vessel dissectors of the present invention both having tip wiping capabilities;

FIGS. 14A-14C are several views of the transverse displacement of an alternative vessel holding tool from an endoscopic vessel harvester of the present invention;

FIGS. 15A-15B are side and perspective views of an alternative vessel holding tool of the present invention having one connecting rod;

FIGS. 16A-16B are side and perspective views of a low profile vessel holding tool of the present invention formed of thin wire;

FIGS. 17A-17B are partial sectional views of alternative vessel holding tools of the present invention incorporating a mechanism for preventing vessel avulsion;

FIG. 18 is a side view of the distal end of an alternative vessel holding tool of the present invention having an enlarged locking member for better positioning of the vessel;

FIGS. 19A and 19B are schematic views of an alternative vessel severing tool of the present invention having wire electrodes extending into an enlarged vessel-receiving gap;

FIG. 20 is a schematic view of an alternative vessel severing tool of the present invention having a stepped vessel receiving gap;

FIGS. 21A-21B are two side views of a vessel severing tool of the present invention having movable jaws;

FIG. 22 is a side view of a vessel severing tool of the present invention having rotary blades incorporated therein;

FIGS. 27A-27B are side elevational and top plan views, respectively, of a further alternative vessel severing/sealing tool that incorporates a movable mandible for capturing a vessel and a mechanical blade for severing it;

FIGS. 28A-28B are two schematic views of a side-opening vessel severing/sealing tool;

FIG. 29 is a longitudinal endoscopic view showing the use of the tool in FIGS. 28A-28B; and FIG. 30 is a top plan view of an alternative severing tool having a ring and concentric coil bipolar electrode structure.

DETAILED DESCRIPTION OF THE PREFERRED EMBODIMENTS

Figure 5A:
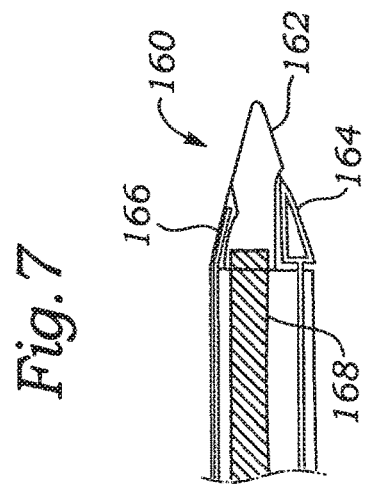
FIG. 5A is a schematic side view of an endoscopic vessel dissector of the prior art passing through body tissue.

The present application provides a number of improvements to prior art vessel harvesting systems. The disclosures herein of various component parts of vessel harvesting systems should be viewed with the presumption that each can work in combination with other components unless stated as being mutually exclusive. For example, the various endoscopic vessel dissectors described herein may be utilized in combination with any of the endoscopic vessel harvesters. Moreover, any single one component improvement described herein may be incorporated into any existing vessel harvesting system, again, unless the structures or functions are mutually exclusive.

Prior Endoscopic Vessel Harvesting System

The three primary components of an exemplary prior art vessel harvesting system are seen in the separate views of FIGS. 1A-1C. This particular system is representative of one type of prior art vessel harvesting systems, and many of the improvements described herein will be described with direct reference to it. However, as will be understood by one of skill in the art, any one single improvement to a subcomponent of the vessel harvesting system may, in most cases, be incorporated into other such systems. More important, if any single improvement(s) are independently claimed, the application should not be construed as being limited to the system shown in FIGS. 1A-1C. That said, the exemplary prior art system includes an endoscopic dissector 20 in FIG. 1A, an endoscopic vessel harvester 22 seen in FIG. 1B, and an access trocar 24 seen in FIG. 1C.

The endoscopic dissector 20 includes an elongated tube or cannula 30 extending between a distal conical tip 32 and a proximal handle 34. A bell-shaped port 36 on a proximal end of the handle 34 receives a conventional medical endoscope 38 which may be fitted with an optical connector 40. Although not shown, the elongated shaft of the endoscope 38 extends through the entire length of the dissector 20 such that a viewing end terminates in proximity to the conical tip 32, which is typically transparent. It should be understood that vessel harvesting systems are typically disposable and are packaged and sold separately from the endoscope which is typically reused. In all cases, however, these endoscopic vessel harvesting systems are designed to accommodate and function with a conventional endoscope, and are therefore claimed accordingly.

Tubing 42 supplies insufflation gas into an input within the handle 34 that opens into an elongated passage within the cannula 30 in communication with a distal egress port 44. In use, the user inserts the distal tip 32 and cannula 30 into the body through an access device such as the trocar 24 seen in FIG. 1C, and into proximity with a target vessel, such as the saphenous vein in the leg. By pushing the conical tip 32 along the target vessel under endoscopic vision, the user is able to grossly dissect connecting tissue from around the vessel. Insufflation gas forced out of the distal port 44 pressurizes the dissected cavity and facilitates viewing and further dissection. After a desired length of target vessel has been separated from surrounding tissue, the dissector 20 is removed from the patient.

Subsequent to vessel dissection, the vessel harvester 22 is inserted through the access trocar 24 and into the dissected cavity around the target vessel. The vessel harvester 22 also includes an elongated tube or cannula 50 extending between an open distal end 52 and a proximal handle 54. Again, a conventional endoscope 38 snaps into a proximal bell-shaped port 56 that includes an axial slot 58 to receive the perpendicularly-extending optical connector 40. As with the dissector 20, the elongated shaft of the endoscope passes entirely through the cannula 50 and terminates at a viewing end or objective lens 60 close to the open distal end 52.

The harvester 22 further includes tools to sever side branches from the target vessel while simultaneously closing them off to prevent bleeding. For instance, a holding tool 62 may be used to manipulate the target vessel so that a severing and sealing tool 64 has clear access to the various side branches. Each of these tools may be manipulated by controls 66 provided in the handle 54. One of the controls 66 is a thumb lever thumb lever that connects to a wiper blade at the distal end of the elongated cannula 50 for clearing the objective lens 60 of the endoscope. To facilitate the harvesting operation, an insufflation system including tubing 68 may be provided so that gas may be passed out the open distal end 52 of the cannula 50. Also, electrical wires 70 connect to the handle 54 to provide energy for a coagulator incorporated into the severing and sealing tool 64. It should be understood that as generally described so far, these components of the prior art vessel harvesting system are well known in the art, the present application dealing with improvements thereto.

The third main component of the harvesting system is the access trocar 24 seen in FIG. 1C. In this embodiment, the trocar includes a main access tube 70 having an angled distal tip 72 and a proximal housing 74. Although not shown, an inner seal such as a diaphragm seal may be incorporated within the housing 74 to provide a gas-tight interface with the dissector 20 or harvester 22 that passes through the trocar 24. The main access tube 70 extends through an incision in the body and a spring-biased clip 76 secures the trocar thereto.

Improvements to Dissection Function

FIG. 2A shows the distal end of an alternative vessel dissector 80 of the present invention including an articulated dissecting tip 82. The tip 82 connects to an elongated cannula 84 via an accordion-like flexible interface or sleeve 86. A pair of pull wires 88 extends through the cannula 84 and attaches to points on opposite sides of the dissecting tip 82. By manipulating the pull wires 88, the user can angle the generally conical tip 82 in either direction within a plane, relative to the axis of the elongated cannula. By rotating the entire cannula 84, a full 360° range of tip movement is obtained. The flexible sleeve 86 acts like a compression spring and tends to revert the tip 82 back to an axial alignment when pull forces are released.

FIG. 2B is another alternative vessel dissector 90 having an articulated dissecting tip 92. As with the dissector 80, the tip 92 connects to the distal end of an elongated cannula 94 in a manner that enables it to be angled within a plane with respect to the cannula. In this embodiment, a spherical bearing surface 96 provides the interface between the tip 92 and cannula 94. A pair of pull wires 98 connected to the tip 92 enables the user to angle the tip as desired. A flexible spine of sorts (not shown) may also be provided to provide a force that restores the axial alignment of the tip 92 when pull forces are released.

FIG. 3 is a side view schematically illustrating the possible path of bodily fluids into an existing endoscopic vessel dissector 100 that includes one or more ports 102 near its distal end for insufflation of gas such as $CO_2$. That is, a passage is provided within the cannula of the vessel dissector 100 to deliver gas from a proximal end thereof to the ports 112. If fluid is permitted to enter the cannula through the insufflation ports 102, it may eventually migrate to within the transparent distal tip and interfere with endoscopic viewing therefrom.

FIG. 4A illustrates the distal end of an alternative vessel dissector 110 of the present invention including a small fluid barrier 112 extending proximally from the distal tip 114 for inhibiting ingress of bodily fluids into insufflation ports 116 formed in the side of the dissector cannula. The fluid barrier 112 in this embodiment comprises a tubular shield which can be formed from relatively thin medical plastics. The fluid barrier 112 is desirably flexible enough to permit gas egress from the ports 116 while preventing liquid or solid ingress, much like a reed valve.

FIG. 4B shows an alternative vessel dissector 120 having an alternative fluid barrier 122 surrounding the distal end thereof near the distal tip 124. The fluid barrier 122 in this embodiment comprises a tubular porous membrane that covers the gas insufflation ports 126 in the side of the dissector cannula so that liquid or solid is prevented from entering though gas can exit. The membrane 122 is any medically suitable gas-permeable liquid-resistant barrier such as ePTFE made by W.L. Gore.

In a further embodiment, the port from which insufflation gas is expelled is located not on the cannula body, but on a dissecting tip secured to the distal end thereof. For example, the dissecting tips 82, 92 of FIG. 2A/2B may feature a port from which gas escapes into the surrounding tissue cavity. Alternatively, a transparent conical tip 32 as in FIG. 1A may have a port formed at the distal apex. In each of these alternatives, a fluid barrier desirably fills or covers the port to prevent liquid or solid ingress, while permitting gas egress. Forming the port on the dissecting tip may be advantageous because the gas is expelled farther distally, and a selection of different tips as desired may be coupled to a generic cannula.

FIG. 5A is a schematic side view of an endoscopic vessel dissector 100 of the prior art passing through body tissue 104. Insufflation assists in maintaining the dissected cavity or tunnel, though there may be friction between tissue and the following cannula 106 because of its equal size relative to the dissecting tip 108.

Figure 5B:
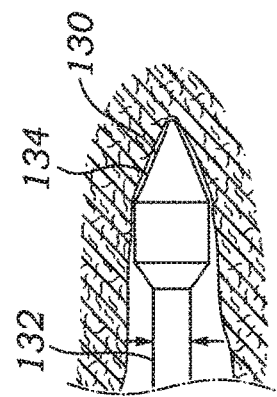
FIG. 5B is a schematic side view of an endoscopic vessel dissector of the present invention having a narrowed cannula for easier passage through body tissue.

To help facilitate passage of the cannula through issue, an endoscopic vessel dissector 130 of the present invention seen in FIG. 5B includes a narrowed cannula 132, at least adjacent to a dissecting tip 134 and desirably along its entire length. The cannula 132 has a diameter that is smaller than the diameter of the dissecting tip 134, and preferably between about 50-75% of the diameter of the dissecting tip 134. A narrow cannula proximal to the dissecting tip improves maneuverability and reduces shaft friction within the dissected tunnel.

Figure 6A:
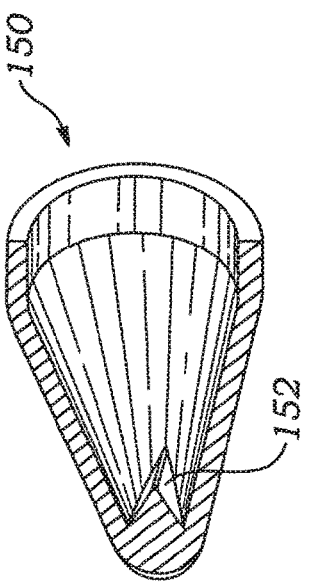
FIGS. 6A-6C are longitudinal sectional views through alternative transparent conical tips for use with endoscopic vessel dissectors of the present invention.
Figure 6B:
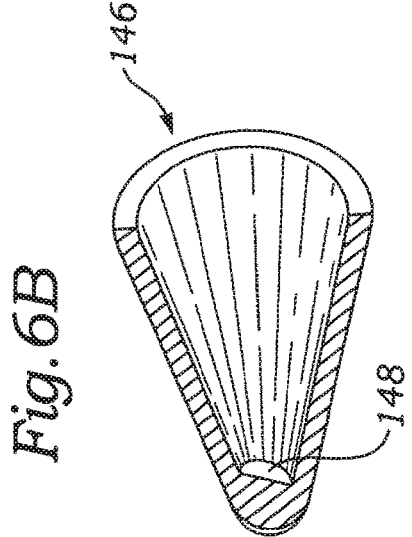
Figure 6C:
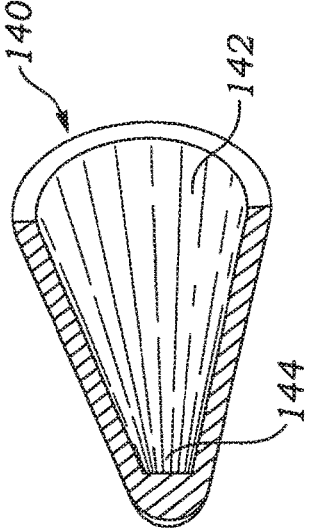

FIGS. 6A-6C are longitudinal sectional views through alternative transparent tips for use with endoscopic vessel dissectors of the present invention. Prior transparent dissection tips, such as seen in U.S. Pat. No. 5,980,549 to Chin, et al., include a hollow interior with a front wall tapering to a sharp point, or apex. The outer profile retains a more rounded, blunt configuration for atraumatic dissection. The sharp inner apex helps remove a spot of distortion in the center of the visual field.

In addition to distortion, some conical blunt dissection tips made of clear materials reflect light from the light fibers back to the objective lens of the endoscope. To address this need, a generally conical dissection tip 140 in FIG. 6A includes an inner tapering surface 142 that terminates at its distal end in a line 144 so as to form an elongated inner corner, or reverse wedge shape. This configuration works to reduce glare back to the objective lens of the endoscope. In FIG. 6B, a dissection tip 146 includes an inner surface that tapers downward toward its distal end and terminates in a flat surface 148 set at an angle from the axis of the tip 146. In this case, incident light is reflected away from the objective lens, which is typically placed along or near the axis of the tip or dissector cannula. Finally, FIG. 6C illustrates a dissection tip 150 having an internal taper that ends at its distal-most extent in a backward wedge. This shape helps deflect light from the fibers outward as opposed to directly backward, thus reducing glare or reflection. All of these shapes have the effect of reducing incident glare from the light fibers back to the objective lens of the endoscope, thus improving the user's view.

Figure 7:
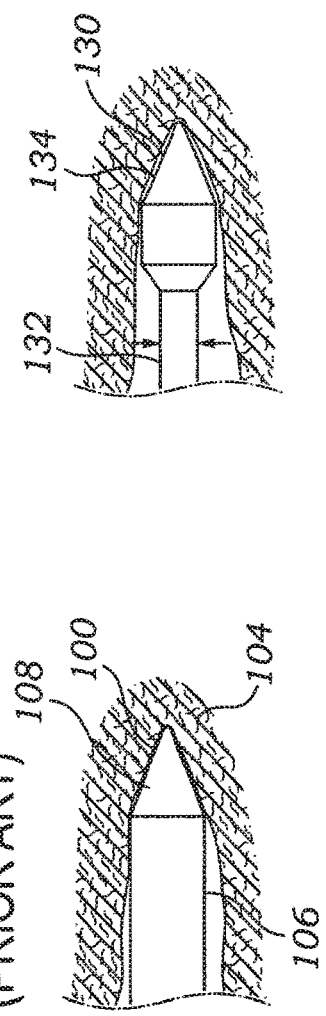
FIG. 7 is a schematic sectional view of the distal end of an alternative endoscopic vessel dissector of the present invention which incorporates tools for harvesting vessels.

A common technique for vessel harvesting is to provide a separate vessel dissector and vessel harvester, with the devices being inserted one at a time in the body, typically through the access trocar. Such is the configuration of the system in FIGS. 1A-1C. However, it is conceivable that the dissecting and harvesting functions can be combined into a single device to save time. For instance, FIG. 7 schematically illustrates the distal end of an integrated endoscopic vessel dissector/harvester 160 of the present invention having a blunt dissecting tip 162 with apertures or recesses for the harvesting tools. More particularly, a vessel holding tool 164 includes a tapered outer surface to match the dissection tip 162 and is stationed within a recess therein. Likewise, a vessel severing tool 166 having an outer surface that conforms to the dissection tip 162 is retracted into a similar recess. Each of the vessel holding tool 164 and vessel severing tool 166 docks into recesses in the dissecting tip and has an exterior shape that conforms to the conical exterior of the dissecting tip so as to match its shape. The distal end of an endoscope 168 is seen extending within the clear dissection tip 162. For dissection, the tools 164, 166 are retracted to conform to the conical tip 162. Then, by manipulating the vessel holding tool 164 and vessel severing tool 166 (such as by axial and rotational movement), selected side branches or primary vessels may be severed and sealed immediately after a section of tunnel around the primary vessel has been dissected. The vessel dissector/harvester 160 is therefore advanced in stages along the primary vessel performing both dissection and side branch management.

Another configuration that is contemplated to combine the functions of the tissue dissector and vessel harvester is to provide a dissection tip that can be detached from a cannula which contains harvesting tools. For example, any of the conical tips seen in FIGS. 6A-6C may be separable from a cannula that houses any of the harvesting tools described below. With such a system the user may alternate between dissection in ligation-transection as desired. Furthermore, such a detachable conical tip may include an opening therethrough to permit $CO_2$ insufflation. Following dissection, the cone is detached and insufflation may continue through the open end of the cannula. Another alternative is to provide a tether connecting the removable conical tip to the cannula. In this way, the tip can be detached the remains in close proximity to the distal end of the cannula for reattachment if desired, Occasionally, fatty or other tissue sticks to the outside of the conical dissecting tip and prevents clear visualization therethrough. FIG. 8 is a perspective view of an endoscopic vessel dissector 170 of the present invention having a wiper blade or finger 172 for clearing the distal dissecting tip 174 of tissue. In this embodiment, the wiper blade 172 pivots about an axis 176 at the beginning of the dissecting tip 174, or end of the cannula 178. An actuating rod 180 controlled by a thumb lever 182 connects to the wiper blade 172 and permits the user to alternately retract and engage the blade with the exterior of the dissecting tip 174. The tip 174 rotates about the axis of the cannula 178 when the user turns a knob 184 at the proximal end of the device. The wiper blade 172 may be rigid or include a resilient scraper much like a vehicle wiper blade. Various structural details of this arrangement are left out but are well within those skilled in the art of medical device design. Likewise, alternative arrangements are contemplated, such as those shown in FIGS. 9 and 10.

FIGS. 9 and 10 are perspective views of the distal tip of two alternative endoscopic vessel dissectors of the present invention both having tip wiping capabilities. The dissector 190 in FIG. 9 is similar to the dissector 170 of FIG. 8 in that it includes a wiper blade or finger 192 for clearing tissue from the conical dissecting tip 194. Instead of the tip rotating, however, the blade 192 swivels about the axis of the device, such as through its connection with a rotating outer sleeve or shaft 196 of the elongated device. Again, details of the actuation of the shaft 196 are not shown, but are easily borrowed or surmised from existing devices. FIG. 10 illustrates a dissector 200 fitted with an O-ring wiper 202 over its conical dissecting tip. An actuation rod 204 displaces the O-ring wiper 202 longitudinally to wipe clean the dissecting tip. The O-ring wiper 202 may be formed as a loosely-wound metal or plastic spiral to facilitate expansion and contraction around the tip. Of course, there are numerous other configurations of wipers that may be displaced over the dissecting tip, the present application only illustrating an exemplary selection.

A further alternative to the tip wiping devices in FIGS. 8-10 is to add an energized cutting electrode to the wiper blade to remove tissue via ablation. That is, instead of or in addition to an inert rigid or resilient blade, a wire or bar electrode may be incorporated to enable clearing of more stubborn tissue via electrocurrency. Although a specific structure is not shown, the reader will understand that any of the wiper elements shown in FIGS. 8-10 may represent such an energized wiper.

Still further, any of the conical tips illustrated herein, including the simple prior art tip seen in FIG. 5A, may be fitted with a system for clearing adhered tissue using fluid expelled from the cannula. For example, an annular opening or a series of separate circumferentially-spaced openings may be provided between the conical tip and cannula, and streams of saline expelled from the openings to knock tissue off the tip. Saline is particularly suitable, although other fluids such as jets of $CO_2$ gas maybe used. The design intent would be to port the fluid so that it flowed distally along the surface of the cone using the Coanda effect in which a stream of fluid or gas will tend to hug a convex contour when directed at a tangent to that surface.

Improvements to Vessel Holding Function

Once the target vessel has been exposed, such as with dissection along its length, endoscopic vessel harvesting involves passing an elongated device under visualization along the vessel to sever and seal side branches. As mentioned above, numerous such systems are currently available, including the system seen in FIG. 1A-1C. In that system, a vessel holding tool manipulates the target vessel such that the side branches are positioned in front of a severing and sealing tool. It is important to present both the side branch and target vessel clearly so that the user does not accidentally cut the target vessel instead of the side branch. Also, it is desirable to retract the target vessel so that the side branch can be cauterized as far away from the target vessel as possible, to minimize risk of damage to the vessel from the cautery tool (thermal spread).

Figure 11A:
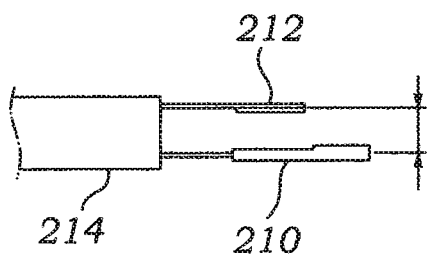
FIGS. 11A and 11B are schematic side views of an endoscopic vessel harvester of the prior art showing vessel holding and severing tools extended from the distal end of a cannula.
Figure 11B:
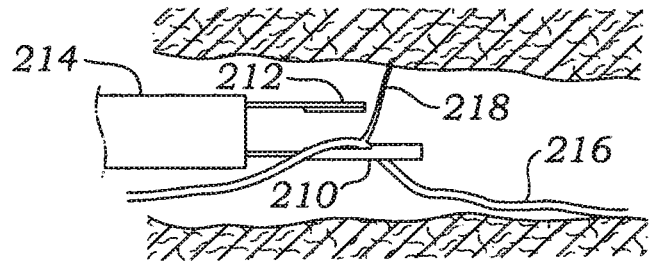

FIGS. 11A and 11B are schematic side views of an endoscopic vessel harvester of the prior art showing a vessel holding tool 210 and a complementary severing tool 212 axially extended from the distal end of a cannula 214. The holding tool 210 typically has a hook or other capturing feature for holding a primary vessel 216. As the device advances, side branches 218 are encountered and the system is manipulated to place them in line with the severing tool 212. There are certain drawbacks to this arrangement, in particular the linear extension of the tools 210, 212, rendering them somewhat awkward to maneuver for proper positioning of the side branches 218.

Figure 12A:
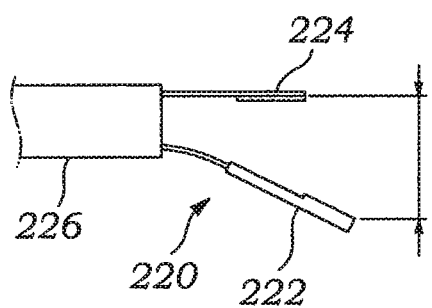
FIGS. 12A and 12B are schematic side views of an endoscopic vessel harvester of the present invention showing vessel holding and severing tools extended from the distal end of a cannula wherein the vessel holding tool translates laterally for better vessel retraction.
Figure 12B:
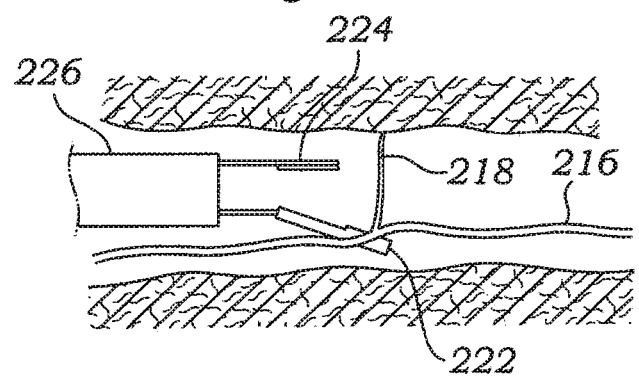

FIGS. 12A and 12B are schematic side views of an endoscopic vessel harvester 220 of the present invention showing a vessel holding tool 222 and a severing tool 224 extended from the distal end of a cannula 226. To more easily accomplish straightening of the side branches 218 in line with the severing tool 224, the vessel holding tool 222 translates laterally. As seen in FIG. 12B, the effect of angling the holding tool 222 radially outward is to facilitate advancement of the tool along the primary vessel 216 as well as to straighten the side branch 218 for more effective cutting with the severing tool 224. A comparison of FIGS. 11A and 12A shows the increase in spacing between the holding and severing tools, which exposes a greater length of side branch. The holding tool 222 can be displaced laterally as shown by simply mounting it on a curved or bent actuation rod, or via an angling mechanism, not shown. In the case of a curved or bent support rod, the rod may be flexible so as to retract within the cannula, and the farther the tool 22 extends the greater the lateral displacement. In general, the vessel holding tool 222 includes a support rod that extends through the elongated cannula 226 and which is angled or is configured to angle laterally at a location close to the distal end of the tool.

Figure 13:
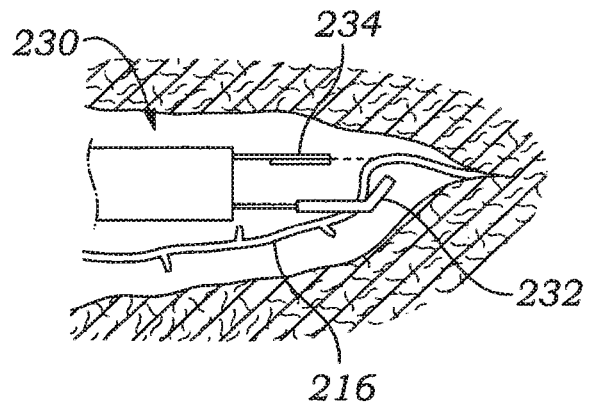
FIG. 13 is a schematic side view of an alternative endoscopic vessel harvester of the present invention wherein a vessel holding tool includes a tip angled toward the vessel severing tool.

FIG. 13 is a schematic side view of an alternative endoscopic vessel harvester 230 of the present invention wherein a vessel holding tool 232 includes a tip angled toward the vessel severing tool 234. In this way, the holding tool 232 can position the primary vessel 216 in line with the severing tool 234. Ultimately, the primary vessel 216 will be severed at at least one end after having been separated from its connecting side branches. The holding tool 232 facilitates this step. It is conceivable that the harvesters 220 and 230 can be combined such that the vessel holding tool may alternately be angled away from the severing tool, as seen in FIG. 12A, and toward the severing tool, as seen in FIG. 13. In other words, an articulating vessel holding tool may be provided that has a support rod extending through the cannula which is configured to articulate laterally at a location close to the distal end of the tool and enable different angulations depending on the situation.

FIGS. 14A-14C are several views of the transverse displacement of an alternative vessel holding tool 240 upon extension from the cannula 242 of an endoscopic vessel harvester of the present invention. In this embodiment, the holding tool 240 mounts on the end of an elastic wireform 244 having a bend 246. When retracted, the wireform 244 straightens within the delivery channel 248. As the tool is extended, the bend 246 eventually clears the end of the channel 248 causing lateral displacement of the holding tool 240.

Another way to enable angling of the distal end of the vessel holding tool is to provide a flexible support rod or wireform and surround it with a rigid hypotube. Both structures may longitudinally extend from the mouth of the cannula, and then retraction of the hypotube from around the wireform angles the vessel holding tool. In this embodiment, greater maneuverability of the vessel holding tube is provided as it may be angled at various axial locations rather than immediately as it exits the cannula.

In a further advantageous feature, the vessel hook of the vessel holding tool may incorporate a tapered blunt distal dissecting surface for blunt dissection of tissue. The term "blunt" surface in this context means one without sharp points or corners and with some degree of taper to facilitate division or partition of tissue planes. For example, the conical tips described herein are considered blunt, and as a rule do not have sharp points. The more rectilinear tissue holders of the prior art, however, are too blunt and not well suited for tissue dissection.

It is very important to minimize obstructions in the field of view—the more the device blocks the user's view of the tissue, the greater the risk of avulsions and cautery mistakes. FIGS. 15A-15B are side and perspective views of an alternative vessel holding tool 250 of the present invention that has a lower profile than previous tools and thus provides greater visibility of its operation. With reference back to FIG. 1B, the holding tool 62 of the prior art includes two rods or supports that extend distally from the cannula 50. These two rods present solid viewing obstacles interposed between the endoscope objective lens and the actual vessel holding operation. Desirably these obstacles are minimized.

In one such lower profile holder, the vessel holding tool 250 has a single main rod or support 252 extending distally from the distal end of the cannula 254 that carries a vessel hook 256. The hook 256 is shaped to partially surround the primary vessel and manipulate it to present a side branch to an associated vessel severing tool (not shown). FIG. 15B illustrates the extension of a locking member 258, which can be, for example, a concentric or telescoping extension of the main rod 252. The hook 256 may be substantially C-shaped so as to partially surround the vessel, and the extension of the locking member 258 closes the remaining open side so that the vessel is completely surrounded and captured therein. In this way, a vessel may be securely held by the holding tool 250 without risk of dislodgment yet the view from the objective lens is maximized by removal of one of the support rods, FIGS. 16A-16B illustrate a further vessel holding tool 260 of the present invention formed of thin wire, also to reduce its profile, reduce impediments to endoscopic viewing, and thus increase visibility and accuracy of the operation. The tool 260 extends from the cannula 262 and includes a hook portion 264 formed of a single wire, and a translating locking member 266 formed of another wire or pin. Again, with the locking member 266 extended the holding tool 260 completely encloses the vessel for manipulation and severing. Although there are two support rods extending from the cannula, they are extremely thin and present a minimum viewing obstacle to the objective lens. Desirably, the holding tool 260 is formed of metal or plastic wires having a thickness of between about 0.5 mm and 1.0 mm.

FIG. 17A is a partial sectional view of a vessel holding tool 270 of the present invention incorporating a mechanism for preventing vessel avulsion. These types of vessel holding tools are used to hook the primary vessel and move down its length, occasionally stopping to sever side branches. If the tool is moved too fast or too hard when a side branch is reached, damage can occur. The tool 270 includes a hook portion 272 that is mounted on the end of a displacement rod 274 extending from the cannula 276. Within the cannula 276, the rod 274 passes through a friction collar 278 that acts as a damped slip mechanism between the hook portion 272 and the cannula 276. That is, if the hook portion 272 experiences resistance as it travels down the length of the primary vessel, further movement of the cannula 276 will not further pull or push on the vessel, but instead will cause damped relative movement between the cannula and the hook portion.

In a similar manner, FIG. 17B shows a vessel holding tool 280 with a hook portion 282 mounted on a displacement rod 284 extending from a cannula 286. A slip mechanism 288, in this case a piston/cylinder/spring arrangement, permits damped relative tool/cannula movement in case the hook portion catches on any body structure and generates a reaction force in the displacement rod 284 in opposition to movement of the cannula 286. Of course, the two examples of FIGS. 17A and 17B are merely exemplary and other clutch mechanisms performing a similar function can be substituted.

Finally, FIG. 18 illustrates still another vessel holding tool 290 of the present invention having an enlarged locking member 292 for better positioning of the vessel 294. That is, the vessel 294 is first retained within the hook portion 296 then a locking member 292 is axially extended to capture it. Earlier locking members were thin rods or pins that left a relatively large space within the mouth of the hook portion 296, and thus especially smaller vessels could easily move around. In this embodiment, the locking member 292 is shaped as a large wedge that limits the space in which the vessel 294 is held and thus increases its stability prior to the side branch severing operation. In terms of relative size, the locking member 292 when extended desirably reduces the space within the mouth of the hook portion 296 by about 50%. The tapered leading edge helps prevent pinching of the vessel as the locking member 292 extends.

Improvements to Vessel Severing Function

Numerous instruments are known which coagulate, seal, join, or cut tissue, and which are suitable, for example, for severing a target vessel from surrounding side branches and securing the separated ends to stanch bleeding. Such devices typically comprise a pair of tweezers, jaws or forceps that grasp onto and hold tissue therebetween. The devices may operate with a heating element in contact with the tissue, with an ultrasonic heater that employs frictional heating of the tissue, or with a mono- or bi-polar electrode heating system that passes current through the tissue such that the tissue is heated by virtue of its own electrical resistance. The devices heat the tissue to temperatures such that the tissue is either "cut" or "sealed", as follows. When tissue is heated in excess of 100° Celsius, the tissue disposed between the tweezers, jaws or forceps will be broken down and is thus, "cut". However, when the tissue is heated to temperatures between 50° to 90° Celsius, the tissue will instead simply "seal" or "weld" to adjacent tissue. Monopolar and bipolar probes, forceps or scissors use high frequency electrical current that passes through the tissue to be coagulated. The current passing through the tissue causes the tissue to be heated, resulting in coagulation of tissue proteins. In the monopolar variety of these instruments, the current leaves the electrode and after passing through the tissue, returns to the generator by means of a "ground plate" which is attached or connected to a distant part of the patient's body. In a bipolar version of such an electro-surgical instrument, the electric current passes between two electrodes with the tissue being placed or held between the two electrodes as in the "Kleppinger bipolar forceps" used for occlusion of Fallopian tubes. A new development in this area is the "Tripolar" instrument marketed by Cabot and Circon-ACMI which incorporates a mechanical cutting element in addition to monopolar coagulating electrodes. A similar combined sealing and mechanical cutting device may also be known as a tissue "bisector," which merges the terms bipolar cautery and dissector. One tissue bisector is packaged for sale as an element of the VASOVIEW® 6 vessel harvesting systems by Guidant Corporation of Santa Clara, Calif. In ultrasonic tissue heaters, a very high frequency (ultrasonic) vibrating element or rod is held in contact with the tissue. The rapid vibrations generate heat causing the proteins in the tissue to become coagulated. Conductive tissue welders usually include jaws that clamp tissue therebetween, one or both of which are resistively heated. In this type of instrument, no electrical current passes through the tissue, as is the case for monopolar or bipolar cautery, It should be understood that any of these prior instruments for severing and/or sealing vessels, or those described below, may be combined with the various components of the vessel harvesting systems described herein. It should also be understood that various configurations of monopolar, bipolar, or other type of electrodes may be provided on the vessel severing/sealing tools described below. Those of skill in the art will understand that the particular shape and size of the electrodes, and their arrangement with respect to other electrodes, will dictate the power requirements and operational constraints. Further, some embodiments described herein may work better with one or other type of electrodes or heating elements, though such optimal permutations will not be exhaustively described.

One important function of any severing tool is to manage vessels of different sizes without extra effort on the part of the user. This is particularly important for bipolar cautery tools which must realize good tissue contact with both electrodes for optimum performance. For fixed electrodes (such as the "bisector" described above), small vessels are more difficult to cauterize; users are taught to position the vessel between the bisector electrodes, and then to rotate the bisector to ensure good contact with both electrodes. Merely decreasing the distance between the electrodes for better contact may prevent use on larger vessels. Moveable electrodes, or jaws, are on solution but require some additional effort to avoid clamping too hard on the vessel, which may result in damage thereto.

FIGS. 19A and 19B are schematic views of an alternative vessel severing tool 300 of the present invention having two wire electrodes 302 overlapping across a large gap G defined by a mouth for receiving a vessel. In contrast with some earlier devices, the gap G is large enough to receive both the side branches and the primary vessel, preferably between about 4.0 mm and 6.0 mm, more preferably about 6.0 mm. The wire electrodes 302 that overlap in a crossing pattern across the gap G are resilient and flex to automatically accommodate widely varying sizes of vessel. In this context "accommodate" means to contact opposite sides of the vessel. This is especially important to ensure good contact with very small vessels. The vessel severing tool 300 desirably accommodates vessels having diameters that range from between 0.5 mm and 6.0 mm. In a variation of the embodiment of FIGS. 19A and 19B, a vessel severing tool has a mouth defined by facing vessel contacts that flex apart upon receiving a vessel therebetween, though the contacts may not be electrodes. Any cutting tool may be combined with a variably-sized mouth to secure different sized vessels.

Desirably, the wire electrodes are made of stainless steel and have a wire thickness of between about 0.5 mm and 1.0 mm so that they easily flex to permit a vessel to move farther into the gap than if they were more rigid and thus ensure good current contact with the vessel. Also, as seen in FIG. 19B, the wire electrodes 302 are set at different radial distances from the central axis of the tool out of contact with each other, thus providing the separation needed for bipolar coagulation. One distinct advantage of the vessel severing tool 300 over prior designs is its ability to automatically accommodate varying sizes of vessel. That is tools having movable jaws, for example, can adapt to various vessel diameters but only upon careful user manipulation. The tool 300 thus speeds up the entire vessel harvesting operation, which may involve severance of numerous vessels, FIG. 20 is a side view of an alternative vessel severing tool 310 of the present invention having a stepped vessel-receiving mouth 312. The stepped shape of the mouth 312 accommodates a wider range of vessel sizes while ensuring good contact with tissue cautery electrodes (not shown) provided, for example, on opposite sides of the mouth. In contrast to a fixed V-shaped gap, the stair-stepped shape of the mouth 312 presents several progressively smaller intermediate gaps with generally parallel sides that provide regions of constant width surface contact with the vessel. Also, the step to the next smaller intermediate gap contacts the vessel. This "bracketing" of the vessel helps ensure a good seal without the risk of excessive pinching. The vessel severing tool 300 desirably accommodates vessels having diameters that range from between 0.5 mm and 6.0 mm. In one embodiment, the mouth 312 of the vessel severing tool 300 defines intermediate gaps having widths in decreasing increments of 1.0 mm, for example 6-5-4 mm, or 5-4-3 mm.

Although immovable severing/sealing tools may prove suitable in certain applications, often it is desirable to apply certain amount of pressure to the vessel with movable jaws, for example. FIGS. 21A-21B illustrate a vessel severing tool 320 of the present invention having jaws 322 that are resiliently biased away from one another and which can be partially closed. The jaws 322 may carry bipolar or monopolar electrodes. A pull wire or control rod 324 connects to a closure ring 326 and enables axial displacement thereof for closing the jaws 322, as seen in FIG. 21B. Visualization of the severing/sealing operation then enables the user to vary the extent of closure of the jaws 322, and thus the magnitude of pressure applied. The jaws 322 cannot completely close and have a minimum gap therebetween as see in FIG. 21B of between about 0.5 mm and 1.0 mm. This minimum is calibrated so that the tool 320 accommodates even the smallest expected vessels, yet excessive clamping of even much larger vessels is reduced because there is no contact between the jaws 322.

FIG. 22 is a side view of a vessel severing tool 330 having stationery jaws 332 and rotary blades 334 incorporated thereon. The blades 334 may be connected to electric power and function as cutting electrodes, or may be inert knife blades, that work in conjunction with separate sealing electrodes (not shown) provided on the jaws 332. This configuration removes the need for providing electrodes that perform dual severing and sealing functions, which frees the designer to optimize the sealing electrodes.

Figure 23A:
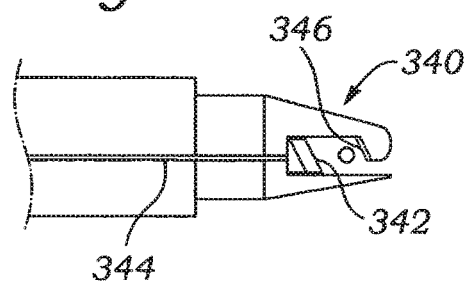
FIGS. 23A-23B are two side views of a vessel severing tool of the present invention having a movable blade.
Figure 23B:
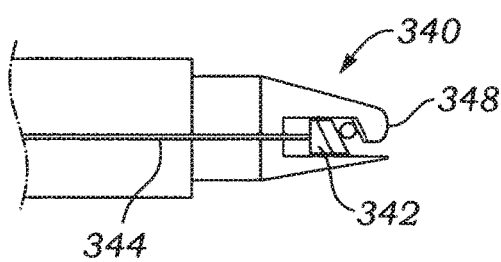

FIGS. 23A-23B are two side views of a vessel severing tool 340 having a movable blade 342 that desirably works in cooperation with electrodes (not shown) that seal the cut vessel. A control rod 344 connects to displace the blade 342 toward an anvil 346 provided on a hook portion 348 of the tool 340. The blade 342 and cooperating anvil 346 are slightly angled as shown to sever the vessel with a shearing action. A mechanical cutter such as this may be desirable in contrast to electrocautery transection which can be time-consuming, may inflict thermal damage on the tissue, and may not be entirely effective.

Figure 24:
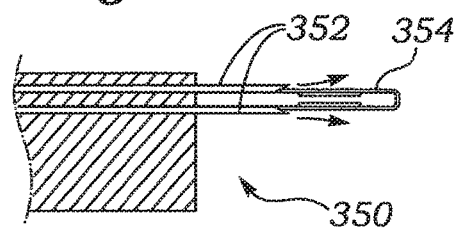
FIG. 24 is a schematic view of a vessel severing tool of the present invention having a system for clearing tissue therefrom using gas jets.

FIG. 24 schematically illustrates a vessel severing tool 350 having a system for clearing tissue therefrom using gas jets. Occasionally, the repeated application of heat or electricity to tissue creates sticking or burning of the tissue to the electrodes. One means to resolve this problem is to provide tubing 352 extending adjacent a severing/sealing tool 354. The tubing 352 terminates close to the electrodes or cutting blades of the tool 354 and jets of gas such as $CO_2$ may be expelled from the open ends or from special nozzles to knock tissue off the tool. $CO_2$ is particularly suitable because it is already used for insufflation of the body cavity, although other fluids such as saline may also be used.

Figure 25A:
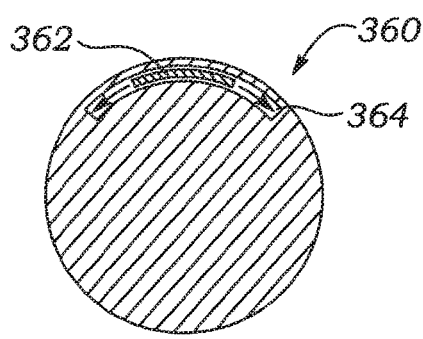
FIGS. 25A-25B are front and top section views, respectively, of an alternative vessel severing tool of the present invention capable of translating transversely as well as longitudinally.
Figure 25B:
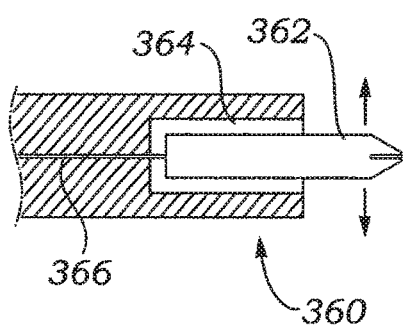

FIGS. 25A-25B are front and top section views, respectively, of an alternative vessel severing tool 360 capable of translating transversely as well as longitudinally. An electrode-carrying member 362 translates circumferentially within an arcuate slot 364, and may be actuated by a control rod 366. This arrangement greatly enhances the maneuverability of the tool and consequently the options for the user.

Figure 26:
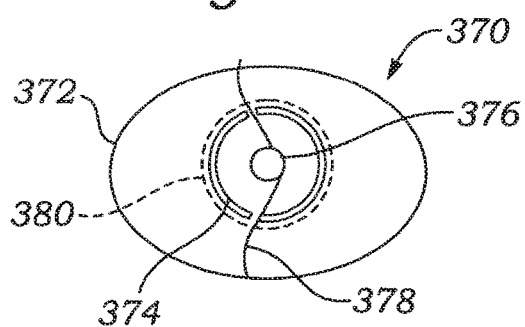
FIG. 26 is a schematic front view of an alternative vessel severing tool of the present invention having a tubular cutting element surrounding a tubular primary vessel shield.

In FIG. 26, a severing/sealing tool 370 shown from its front end within an insufflated tunnel 372 includes a cannula having a pair of partial tubular vessel shields 374 extending therefrom around a primary vessel 376. The gaps between the shields 374 accommodate side branches 378 from the primary vessel 376. A tubular cutting element 380 that may be axially displaced from the cannula surrounds the shields 374. The user positions the shields around a vessel 376 with the side branches 378 as shown, and then advances the cutting element 380. The shields 374 protect the vessel 376 and ensure adequate stump length of the transected branches 378. The cutting element 380 may be a tubular knife blade or an electrode designed to cut.

FIGS. 27A-27B are side and top views of a vessel severing/sealing tool 400 that incorporates several moving parts. The tool 400 includes a pair of fork-shaped electrodes 402 spaced laterally apart so as to create a gap within which moves a severing blade 404. A vessel capturing mandible 406 also moves within the gap between the electrodes 402. In use, a vessel 408 is seen positioned within the tines of the fork-shaped electrodes 402 and prior to capture by the mandible 406. The mandible 406 has a serrated distal finger to securely capture the target vessel within the tines. Upward movement of the mandible traps the vessel 408 at which time energy may be applied by the electrodes 402 to begin the coagulation process. Subsequently, the blade 404 actuates downward and severs the vessel 408. Mechanisms for moving both the blade 404 and mandible 406 are not shown, although both have angled or arcuate proximal surfaces that can be utilized to cam against a delivery cannula and displace the elements toward one another upon their proximal retraction using a control rod, for example.

FIGS. 28A-28B are two schematic views of a vessel severing/sealing tool 420 incorporating a side-opening cutter/sealer 422. In the enlarged view of FIG. 28B, the cutter 422 comprises an upper electrode 424 and a lower electrode 426 separated across a slot 428. The upper and lower electrodes 424, 426 may be bipolar, and the slot 428 may accommodate a knife blade or other such cutting device. FIG. 29 is an endoscopic view showing the use of the tool 420 severing a side branch 430 from a primary vessel 432.

Finally, FIG. 30 is a top plan view of an alternative severing tool 440 which has a first ring-shaped electrode 442 extending from a cannula structure 444, and the second coil-shaped electrode 446 concentrically arranged around the first electrode.

While the invention has been described in its preferred embodiments, it is to be understood that the words which have been used are words of description and not of limitation. Therefore, changes may be made within the appended claims without departing from the true scope of the invention.

What is claimed is:

1. A vessel dissector that is used in conjunction with an endoscope, comprising:
   an elongated cannula including a lumen therein for receiving the endoscope;
   a blunt dissecting tip provided on a distal end of the elongated cannula that permits an operator of the vessel dissector to dissect tissue while viewing internal body structures via an objective lens of the endoscope; and
   a vessel severing tool extending through at least a portion of the elongated cannula, wherein the vessel severing tool is translatable longitudinally relative to the elongated cannula, and wherein the vessel severing tool comprises an electrode-carrying member that is translatable circumferentially within an arcuate slot extending through an outer surface of the vessel dissector, wherein the arcuate slot comprises an inner radius and an outer radius and a central radius, wherein the outer radius is greater than the inner radius and the central radius is located halfway between the outer radius and the inner radius so that the arcuate slot provides a uniform opening through which the electrode-carrying member is controllable to extend and retract, wherein the electrode-carrying member has an arcuate cross section, and the arcuate cross section of the electrode-carrying member matches an arc of the central radius and movement of the electrode-carrying member in the arcuate slot is constrained to follow the arc of the central radius.

2. The vessel dissector of claim 1, wherein the vessel severing tool further comprises a control rod disposed to actuate the electrode-carrying member.

3. The vessel dissector of claim 2, wherein the blunt dissecting tip has a central axis and the arcuate slot extends along a longitudinal axis that is offset from the central axis of the blunt dissecting tip.

4. The vessel dissector of claim 1, wherein the electrode-carrying member comprises bipolar electrodes.

5. The vessel dissector of claim 4, wherein the vessel severing tool further comprises a control rod disposed to actuate the electrode-carrying member.

6. The vessel dissector of claim 1, wherein the blunt dissecting tip has a central axis and the arcuate slot extends along a longitudinal axis that is offset from the central axis of the blunt dissecting tip.

7. A vessel dissector that is used in conjunction with an endoscope, comprising:
   an elongated cannula including a lumen therein for receiving the endoscope;
   a blunt dissecting tip provided on a distal end of the elongated cannula that permits viewing of internal body structures while an operator of the vessel dissector dissects tissue with the blunt dissecting tip; and
   a vessel severing tool extending through at least a portion of the elongated cannula, wherein the vessel severing tool is translatable longitudinally relative to the elongated cannula, and wherein the vessel severing tool comprises an electrode-carrying member that is translatable circumferentially within a curved slot extending through an outer surface of the vessel dissector, wherein the curved slot is defined by a first wall having an inner radius, a second wall having an outer radius, a third wall connecting one end of the first wall to one end of the second wall, and a fourth wall connecting a second end of the first wall to a second end of the second wall, wherein the outer radius is greater than the inner radius and a central radius is located midway between the outer radius and the inner radius so that the curved slot provides an opening through which the electrode-carrying member is controllable to extend and retract, wherein circumferential translation of the electrode-carrying member is limited to a path extending along only the central radius.

8. The vessel dissector of claim 7, wherein the electrode-carrying member has an arcuate cross section that matches an arc of the central radius.

9. The vessel dissector of claim 8, wherein the vessel severing tool further comprises a control rod disposed to actuate the electrode-carrying member.

10. The vessel dissector of claim 7, wherein the blunt dissecting tip has a central axis and the curved slot extends along a longitudinal axis that is offset from the central axis of the blunt dissecting tip.

11. The vessel dissector of claim 7, wherein the electrode-carrying member comprises bipolar electrodes.

12. The vessel dissector of claim 7, wherein the curved slot is an arcuate slot.

13. The vessel dissector of claim 12, wherein the arcuate slot has a uniform width.

14. The vessel dissector of claim 7, wherein the curved slot is a bow-shaped slot that has a uniform width.

15. The vessel dissector of claim 7, wherein the curved slot has a uniform width.

16. The vessel dissector of claim 7, wherein the blunt dissecting tip has a central axis and the curved slot extends along a longitudinal axis that is offset from the central axis of the blunt dissecting tip, and wherein the curved slot has a uniform width.

* * * * *